(12) United States Patent
Umezawa et al.

(10) Patent No.: US 9,701,841 B2
(45) Date of Patent: *Jul. 11, 2017

(54) CELL PERMEABLE, FLUORESCENT DYE

(71) Applicant: ECOLE POLYTECHNIQUE FEDERALE DE LAUSANNE (EPFL), Lausanne (CH)

(72) Inventors: Keitaro Umezawa, Tokyo (JP); Lukinavicius Grazvydas, Renens (CH); Kai Johnsson, Neuchatel (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,772

(22) Filed: Apr. 19, 2016

(65) Prior Publication Data

US 2016/0230011 A1    Aug. 11, 2016

Related U.S. Application Data

(62) Division of application No. 14/241,152, filed as application No. PCT/EP2011/064750 on Aug. 26, 2011, now Pat. No. 9,346,957.

(51) Int. Cl.
| | |
|---|---|
| C09B 57/00 | (2006.01) |
| C07F 7/08 | (2006.01) |
| C09B 11/24 | (2006.01) |
| G01N 33/58 | (2006.01) |
| C09B 69/00 | (2006.01) |
| C07F 7/10 | (2006.01) |
| C09B 11/28 | (2006.01) |

(52) U.S. Cl.
CPC .............. *C09B 57/00* (2013.01); *C07F 7/081* (2013.01); *C07F 7/10* (2013.01); *C09B 11/24* (2013.01); *C09B 11/28* (2013.01); *C09B 69/008* (2013.01); *G01N 33/582* (2013.01)

(58) Field of Classification Search
CPC ...................................................... C09B 57/00
USPC ............................................................ 540/4
See application file for complete search history.

(56) References Cited

U.S. PATENT DOCUMENTS

| 6,828,159 B1 | 12/2004 | Drexhage et al. |
| 6,849,315 B2 | 2/2005 | Lehmann et al. |
| 2011/0177619 A1 | 7/2011 | Metters et al. |

FOREIGN PATENT DOCUMENTS

| WO | 97/19938 A1 | 6/1997 |
| WO | 2010/126077 A1 | 11/2010 |

OTHER PUBLICATIONS

Egawa et al., "Development of a Far-Red to Near-Infrared Fluorescence Probe for Calcium Ion and its Application to Multicolor Neuronal Imaging", J. Am. Chem. Soc., published Aug. 9, 2011 [3 Pages].

Koide et al., "Evolution of Group 14 Rhodamines as Platforms for Near-Infrared Fluorescence Probes Utilizing Photoinduced Electron Transfer", ACS Chem. Biol. 2011, 6, pp. 600-608, published Mar. 4, 2011 [9 Pages].

(Continued)

*Primary Examiner* — Taofiq A Solola
(74) *Attorney, Agent, or Firm* — Davis & Bujold PLLC; Michael J. Bujold

(57) ABSTRACT

The invention pertains to a near-infrared fluorescent dye that is cell permeable and can be attached to selected proteins in living cells. The dye has the general formula (I)

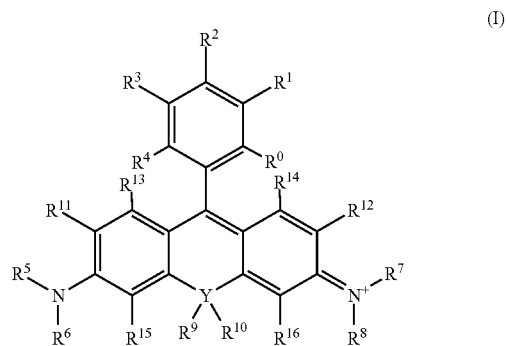

or its corresponding spirolactone (II)

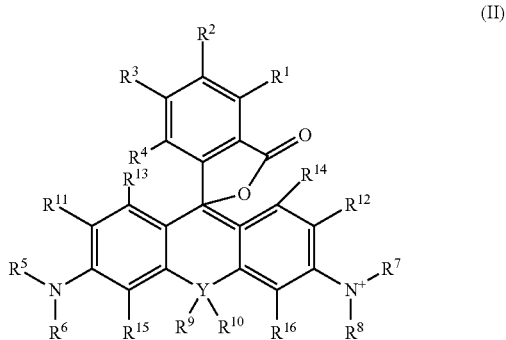

wherein
Y is chosen from the group consisting of Si, Ge and Sn;
$R^0$ is —COO⁻ or COOH;
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are substituents, including hydrogen, independently from each other.
The dye (i) absorbs and emits light at wavelengths above 600 nm; (ii) possesses high photostability; (iii) has high extinction coefficients and high quantum yields; (iv) can be derivatized with different molecules; and (v) is membrane-permeable and shows minimal background binding to biomolecules and biomolecular structures.

25 Claims, 2 Drawing Sheets

(56) References Cited

OTHER PUBLICATIONS

Koide et al., "Development of an Si-Rhodamine-Based Far-Red to Near-Infrared Fluorescence Probe Selective for Hypochlorous Acid and Its Applications for Biological Imaging", J. Am. Chem. Soc. 2011, 133, pp. 5680-5682, published Mar. 28, 2011 [3 Pages].

King et al., "Biososteres, Conformational Restriction, and Prodrugs—Case History: An Example of a Conformational Restriction Approach", Med. Chem: Principle and Practice (1994), pp. 206-209 [3 Pages].

Lukinavičius et. al., "A near-infrared fluorophore for live-cell super-resolution microscopy of cellular proteins"; Nature Chemistry, vol. 5, pp. 132-139, Feb. 2013.

Lukinavičius et. al., "Fluorogenic probes for live-cell imaging of the cytoskeleton"; Nature Methods, vol. 11, pp. 731-733, Jul. 2014.

Iain Johnson and Michelle T.Z. Spence, The Molecular Probes Handbook: A Guide to Fluorescent Probes and Labeling Technologies, edited by Life Technologies Corporation, 11th edition, Ch. 4 & 11, 2010.

Grimm et al., "Synthesis of a Far-Red Photoactivatable Silicon-Containing Rhodamine for Super-Resolution Microscopy", Angew. Chem., Int. Ed., 55, pp. 1723-1727, 2016.

Greg T. Hermanson, "Bioconjugate Techniques" (Second Edition), Ch. 9 & 11, Academic Press, New York, 2008.

Kada, et. al., "Accurate measurement of avidin and streptavidin in crude biofluids with a new, optimized biotin-fluorescein conjugate", Biochimica et Biophysica Acta (BBA)—General Subjects, vol. 1427, Issue 1, pp. 33-43, 1999.

Calloway et. al. "Optimized Fluorescent Trimethoprim Derivatives for in vivo Protein Labeling."; ChemBioChem, vol. 8, pp. 767-774; 2007.

Keppler et al., "A general method for the covalent labeling of fusion proteins with small molecules in vivo", Nature Biotechnology, vol. 21, pp. 86-89, Jan. 2003.

Wang et al., "A general approach to spirolactonized Si-rhodamines", Chem. Commun., vol. 50, pp. 14374-14377, 2014.

Kolmakov et al., "Far-Red Emitting Fluorescent Dyes for Optical Nanoscopy: Fluorinated Silicon-Rhodamines (SiRF Dyes) and Phosphorylated Oxazines", Chem. Eur. J., vol. 21, pp. 13344-13356, 2015.

CELL PERMEABLE, FLUORESCENT DYE

The invention pertains to the field of fluorescent dyes, in particular to cell permeable fluorescent dyes.

BACKGROUND OF THE INVENTION

Synthetic fluorophores are important tools in chemistry and biology. One of the main applications is their use as molecular probes in biomolecular imaging (Lavis, L. D.; Raines, R. T. ACS Chem Biol 2008, 3, 142). The ideal fluorophore for applications in biomolecular imaging should fulfill at least the following five criteria: First, the fluorophore absorbs and admits light at long wavelengths, preferentially above 600 nm. This ensures minimal phototoxicity when exciting the fluorophore, reduces background from cellular autofluorescence and increases tissue penetration for in vivo applications. Second, the fluorophore should possess high photostability to avoid rapid bleaching in the course of an experiment. Third, the fluorophore should be very bright, that is it should possess high extinction coefficients and high quantum yields. Fourth, a derivatization of the fluorophore with (i) reactive groups such as activated esters, (ii) ligands that specifically bind to other (bio)molecules in vitro or in vivo or (iii) molecules that can control the fluorescence properties of the fluorophore should be possible. Fifth, the fluorophore should be membrane permeable and show minimal background binding to biomolecules and biomolecular structures. While numerous fluorophores exist that fulfill the first four criteria, the cyanine fluorophore Cy5 being an example, there are few fluorophores available that also fulfill the fifth criterion.

Recently, a new class of fluorophores have been introduced which are based on the rhodamine structure but in which the oxygen atom in the xanthene ring has been replaced by silicon (Si-rhodamine) or germanium (Ge-rhodamine); cf. FIG. 1 (Xiao, Y.; Fu, M. 2008; CN 1810812. Fu, M.; Xiao, Y.; Qian, X.; Zhao, D.; Xu, Y. Chem Commun (Camb) 2008, 1780. Nagano, T.; Urano, Y.; Koide, Y. 2010; WO 2010126077, p 35. Koide, Y.; Urano, Y.; Hanaoka, K.; Terai, T.; Nagano, T. ACS Chem Biol 2011, 6, 600. Koide, Y.; Urano, Y.; Hanaoka, K.; Terai, T.; Nagano, T. J Am Chem Soc 2011, 133, 5680. Egawa, T.; Koide, Y.; Hanaoka, K.; Komatsu, T.; Terai, T.; Nagano, T. Chem Commun (Camb) 2011, 47, 4162):

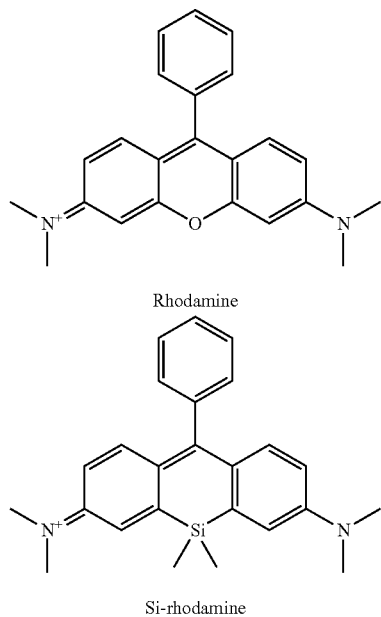

Rhodamine

Si-rhodamine

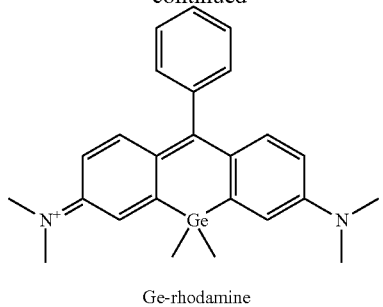

Ge-rhodamine

These fluorophores show a large bathochromic shift relative to regular rhodamine derivatives with excitation and emission wavelengths above 600 nm. At the same time, they have high solubility, are very bright and photostable. In addition, there have been reports on their use in biomolecular imaging (Koide, Y.; Urano, Y.; Hanaoka, K.; Terai, T.; Nagano, T. ACS Chem Biol 2011, 6, 600. Koide, Y.; Urano, Y.; Hanaoka, K.; Terai, T.; Nagano, T. J Am Chem Soc 2011, 133, 5680. Egawa, T.; Koide, Y.; Hanaoka, K.; Komatsu, T.; Terai, T.; Nagano, T. Chem Commun (Camb) 2011, 47, 4162. Egawa, T. et al., J. Am. Chem. Soc, Epub ahead of print, DOI: 10.1021/ja205809h).

The specific coupling of fluorophores to proteins in living cells is an important method in life sciences. Such a specific coupling of fluorophores can be achieved by expressing the protein of interest as a fusion protein with an additional polypeptide that mediates the labeling of the fusion protein with the fluorophore (for review on labelling methods cf. Hinner, M. J.; Johnsson, K. Curr Opin Biotechnol 2010, 21, 766). Numerous approaches exist for achieving such a specific labeling in vitro and in vivo. Examples for such tags are small peptides that tightly bind to other molecules, proteins that tightly bind to other molecules, proteins that undergo a covalent reaction with other molecules and peptides to which other molecules are coupled with the help of enzymes. Methods that have been shown of particular utility for the labeling of intracellular protein are the tetracysteine tag that binds to biarsenical fluorophores, the SNAP-tag that irreversibly reacts with benzylguanine (BG) derivatives (Keppler, A.; Gendreizig, S.; Gronemeyer, T.; Pick, H.; Vogel, H.; Johnsson, K. Nat Biotechnol 2003, 21, 86), the CLIP-tag that reacts with benzylcytosine derivatives, the Halo-tag that reacts with primary chlorides and dihydrofolate reductase that binds to trimethoprim derivatives (Hinner, M. J.; Johnsson, K. Curr Opin Biotechnol 2010, 21, 766). Alternatively, a specific fluorescence labeling of a protein of interest can be achieved through the incorporation of an unnatural, fluorescent amino acid (Liu, C. C.; Schultz, P. G. Annu Rev Biochem 2010, 79, 413). While numerous fluorophores with excitation and emission maxima below 600 nm have been selectively coupled to intracellular proteins using one of the methods described above, the coupling of fluorophores to proteins with excitation and emission maxima above 600 nm remains problematic due to the membrane impermeability of such fluorophores and usually requires the introduction of the fluorophore into the cell through invasive methods such as microinjection (Keppler, A.; Arrivoli, C.; Sironi, L.; Ellenberg, J. Biotechniques 2006, 41, 167), bead-loading (Maurel, D.; Banala, S.; Laroche, T.; Johnsson, K. ACS Chem Biol 2010, 5, 507) or electroporation (Jones, S. A.; Shim, S. H.; He, J.; Zhuang, X. Nat Methods 2011, 8, 499).

BRIEF SUMMARY OF THE INVENTION

A new class of Si-rhodamine derivatives is described (sometimes referred to hereinafter as Si- and Ge-carboxy-rhodamines, respectively) that (i) absorb and admit light at wavelengths above 600 nm; (ii) possess high photostability; (iii) have high extinction coefficients and high quantum yields; (iv) can be derivatizated with different molecules; and (v) are membrane-permeable and show minimal background binding to biomolecules and biomolecular structures. The general structure of the new Si- and Ge-carboxy-rhodamine derivatives is exemplarily shown below:

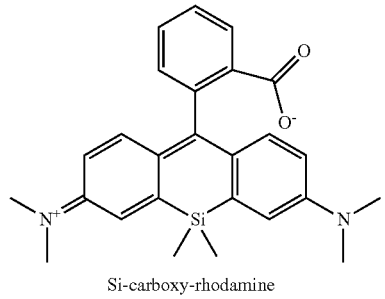

Si-carboxy-rhodamine

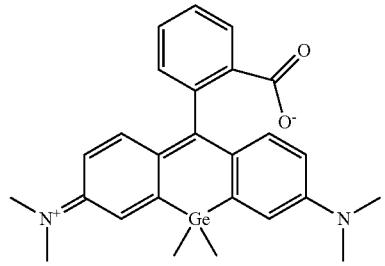

Ge-carboxy-rhodamine

An important feature of these fluorophores is the presence of a carboxyl group at the 2-position of the benzyl ring which dramatically increases membrane permeability and opens up various applications in biomolecular imaging. The carboxyl group permits the formation of a spirolactone, as outlined in more detail hereinafter.

For the avoidance of doubt, it is to be noted that compounds of the invention may be differently charged, e.g. due to pH changes. Moreover, compounds of the invention may be provided in zwitterionic structure or may comprise counterions. None of the aforementioned derivates shall be deemed to be out of the scope of invention.

As an example, the benzylguanine derivative of Si-carboxy-rhodamine (BG-Si-carboxy-rhodamine) for labeling of SNAP-tag fusion proteins in living cells was prepared (SiR650-6BG; cf Section B.3 hereinbelow):

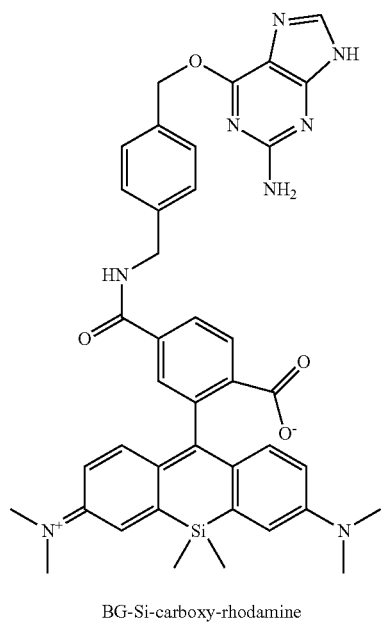

BG-Si-carboxy-rhodamine

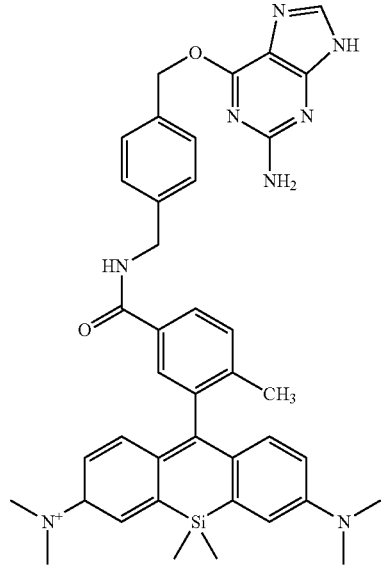

BG-Si-rhodamine
(comparative example)

BG-Si-carboxy-rhodamine possesses excellent membrane permeability and permits the specific labeling of SNAP-tag fusion proteins (the SNAP-tag technology as such is known in the art and suitable ready-to-use kits are commercially available from New England BioLabs, Inc.) in mammalian cells by simply incubating cells with BG-Si-carboxy-rhodamine, as demonstrated by fluorescence imaging. In contrast, the derivative with a methyl group at the 2-position of the benzyl ring (BG-Si-rhodamine) does not permit the specific labeling of SNAP-tag fusion proteins in living cells. This demonstrates the superior permeability and biocompatibility of the Si-carboxy-rhodamine derivatives. Importantly, the use of Si-carboxy-rhodamine derivatives is not limited to the labeling of SNAP-tag fusion proteins but can also be employed for the labeling of Halo-tag and Clip-tag fusion proteins. This demonstrates that Si-carboxy-rhodamine represent a unique platform for the development of fluorescent probes for biomolecular imaging, in which the Si-carboxyrhodamine cores structure is derivatized with: (i) reactive groups such as activated esters, (ii) ligands that specifically bind to other (bio)molecules in vitro or in vivo or (iii) molecules that can control the fluorescence properties of the fluorophore. An example for molecules that can control the fluorescence properties of the fluorophore are calcium indicators or substrates of enzymes.

DETAILED DESCRIPTION OF THE INVENTION

Figure 1:
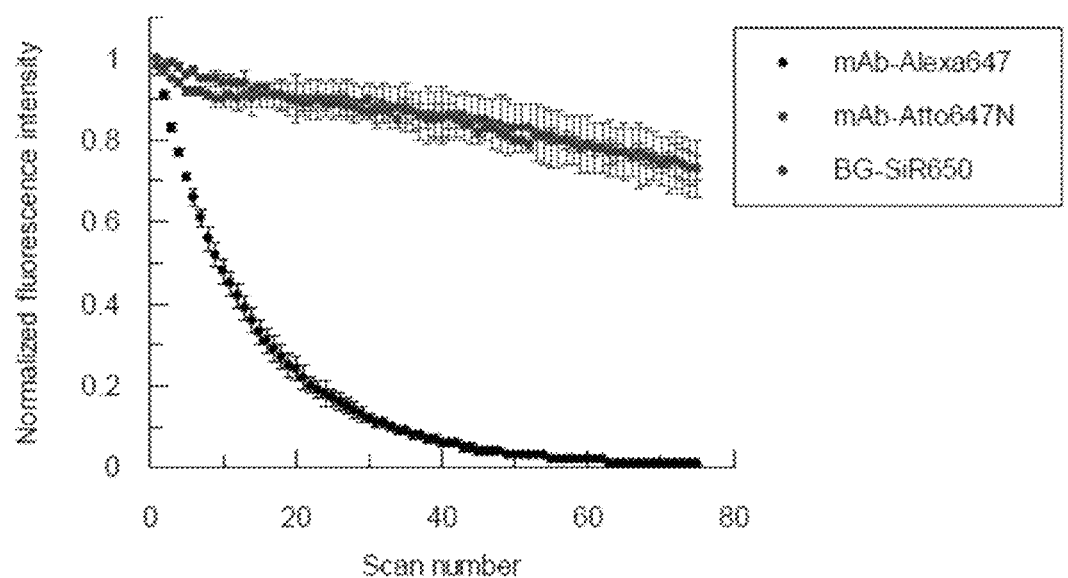
FIG. 1: Comparative fluorescent intensity studies of two prior art dyes and a compound according to the invention.

In general terms, the invention pertains to a compound of formula

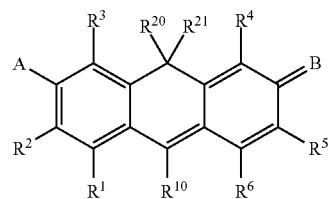

(I)

or its corresponding spirolactone

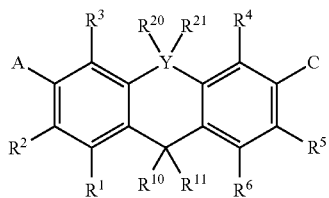

(II)

wherein:
Y is chosen from the group consisting of Si, Ge and Sn;
$R^1$, $R^2$, $R^3$, $R^4$, $R^5$, $R^6$, $R^{29}$ and $R^{21}$ are independently any kind of substituents;
A is $NR^8R^9$, wherein $R^8$ and $R^9$ are independently any kind of substituents;
B is O or $N^+R^{18}R^{19}$, wherein $R^{18}$ and $R^19$ are independently any kind of substituents;
C is $NR^{18}R^{19}$;
$R^{10}$ of (I) has the substructure

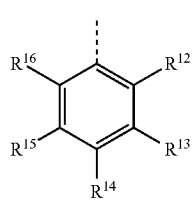

(III)

wherein
one of $R^{12}$ or $R^{16}$ or both is/are independently a carboxylic acid or a salt of a carboxylic acid; and
$R^{13}$, $R^{14}$, $R^{15}$ and optionally one of $R^{12}$ or $R^{16}$ are independently any kind of substituents;
either $R^{12}$ or $R^{16}$ of $R^{10}$ in combination with $R^{11}$ of (II) forms a γ-spirolactone, such that $R^{12}$ of $R^{10}$ in combination with $R^{11}$ of (II) forms the γ-spirolactone (IIa):

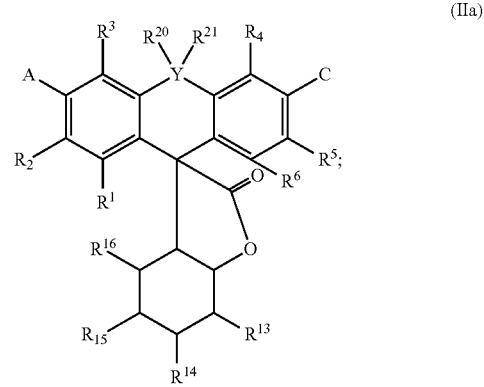

(IIa)

or, alternatively, $R^{16}$ of $R^{10}$ in combination with $R^{11}$ of (II) forms the γ-spirolactone (IIb):

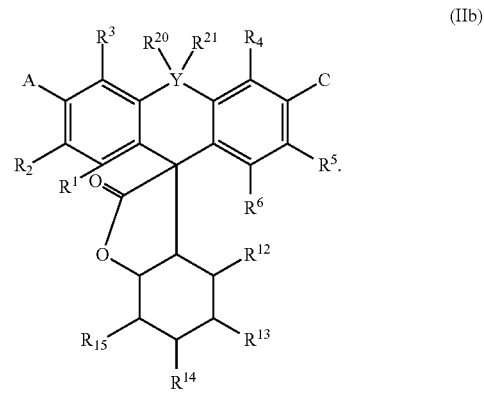

(IIb)

Preferably, $R^1$, $R^2$, $R^3$, $R^4$, $R^5$ and $R^6$ are hydrogen; $R^{20}$ and $R^{21}$ preferably are $C_1$-$C_6$ alkyl, either saturated or unsaturated, most preferably methyl.
In further preferred embodiments of the compounds according to the invention,
$R^1$, $R^2$, $R^3$, $R^4$, $R^5$, $R^6$, $R^{20}$ and $R^{21}$ are independently hydrogen; $C_1$-$C_6$ alkyl, $C_1$-$C_6$ alkoxy, or aryl, wherein the alkyl, alkoxy, or aryl portions have one or more substituents chosen from the group consisting of F, Cl, Br, I;
A is $NR^8R^9$, wherein
$R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, wherein each aforementioned alkyl is optionally substituted with F, amino, hydroxyl, a carboxylic acid, a salt of a carboxylic acid, or a carboxylic acid ester or a $C_1$-$C_6$ alkyl; or
$R^8$ in combination with $R^9$ forms a five- or six-membered heterocyclic substructure chosen from the group consisting of piperidines, morpholines, pyrrolidines or piperazines, wherein each of the aforementioned heterocyclic substructures is optionally substituted by methyl, F, a carboxylic acid, a salt of a carboxylic acid or a carboxylic acid ester or a $C_1$-$C_6$ alkyl; or one of $R^8$ or $R^9$ in combination with $R^2$ forms a five- or six-membered ring substructure, saturated or unsaturated, which is optionally substituted by one or more $C_1$-$C_6$ alkyl or $CH_2SO_3X$, wherein X is H or a counterion; and/or one of $R^8$ or $R^9$ in combination with $R^3$ forms a five- or six-membered ring substructure, saturated or unsaturated, which is optionally substituted by one or more $C_1$-$C_6$ alkyl, F or $CH_2SO_3X$, wherein X is H or a counterion;

B is O or $N^+R^{18}R^{19}$, wherein $R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, wherein each aforementioned alkyl is optionally substituted with F, amino, hydroxyl, a carboxylic acid, a salt of a carboxylic acid, or a carboxylic acid ester or a $C_1$-$C_6$ alkyl; or $R^{18}$ in combination with $R^{19}$ forms a five- or six-membered heterocyclic substructure chosen from the group consisting of piperidines, morpholines, pyrrolidines or piperazines, wherein each of the aforementioned heterocyclic substructures is optionally substituted by F, methyl, a carboxylic acid, a salt of a carboxylic acid or a carboxylic acid ester or a $C_1$-$C_6$ alkyl; or one of $R^{18}$ or $R^{19}$ in combination with $R^5$ forms a five- or six-membered ring substructure, saturated or unsaturated, which is optionally substituted by one or more $C_1$-$C_6$ alkyl or $CH_2SO_3X$, wherein X is H or a counterion; and/or one of $R^{18}$ or $R^{19}$ in combination with $R^4$ forms a five- or six-membered ring substructure, saturated or unsaturated, which is optionally substituted by one or more $C_1$-$C_6$ alkyl, F or $CH_2SO_3X$, wherein X is H or a counterion;

C is $NR^{18}R^{19}$;

in substructure (III)

one of $R^{12}$ or $R^{16}$ or both is/are independently a carboxylic acid or a salt of a carboxylic acid, or sulfonic acid or a salt of a sulfonic acid; and $R^{13}$, $R^{14}$ and $R^{15}$ are independently H, F, Cl, Br, I, $SO_3X$, a carboxylic acid, a salt of a carboxylic acid, an ester of a carboxylic acid, an amide, CN, nitro, hydroxyl, azido, amino, hydrazino; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, $C_6$-$C_{18}$ arylcarboxamido, wherein the alkyl portion(s) of each of the aforementioned is/are optionally substituted one or more times with F, Cl, Br, I, hydroxy, a carboxylic acid, a salt of a carboxylic acid, a carboxylic ester of a $C_1$-$C_6$ alcohol, —$SO_3X$, amino, $C_1$-$C_6$ alkylamino, $C_2$-$C_{12}$ dialkylamino, $C_1$-$C_6$ alkoxy; and/or optionally comprise one or more alkenyl and/or alkynyl moieties; or at least one pair of adjacent substituents $R^{13}$ and $R^{14}$, or $R^{14}$ and $R^{15}$, when taken in combination, forms a fused six-membered aromatic substructure that is optionally further substituted by a carboxylic acid or a salt of a carboxylic acid;

either $R^{12}$ or $R^{16}$ of $R^{10}$ in combination with $R^{11}$ of (II) forms a γ-spirolactone.

In accordance with further preferred embodiments, $R^8$ or $R^9$ in combination with $R^2$ forms substructure

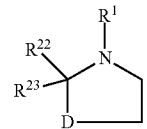

(IV)

wherein

R' denotes the respective one of $R^8$ and $R^9$ which is not incorporated into the ring of substructure (IV);

$R^{22}$ and $R^{23}$ are independently hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl substituents;

D represents O; S; Se; Te; or preferably —$C(R^{24})(R^{25})$—, with $R^{24}$ and $R^{25}$ being independently chosen from the group consisting of hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl substituents.

Similarly to what has been outlined above with respect to substructure (IV), further preferred embodiments of the invention are compounds, wherein $R^{18}$ or $R^{19}$ in combination with $R^5$ forms substructure

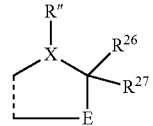

(V)

wherein

R" denotes the respective one of $R^{18}$ and $R^{19}$ which is not incorporated into the ring of substructure (V);

$R^{26}$ and $R^{27}$ are independently hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl radicals;

E represents O; S; Se; Te; or preferably —$C(R^{28})(R^{29})$—, with $R^{28}$ and $R^{29}$ being independently chosen from the group consisting of hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl.

More specifically, currently preferred embodiments of the invention are the following compounds:

(VI)

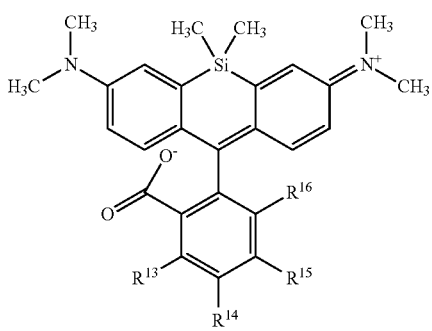

such that the corresponding spirolactone (VIa) is:

(VIa)

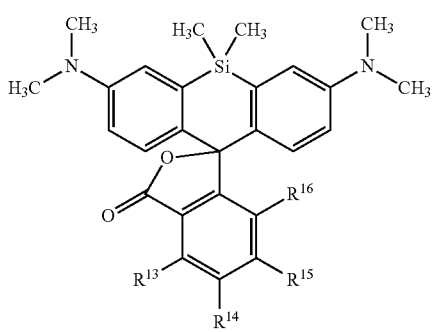

with $R^{13}$, $R^{14}$, $R^{15}$ and $R^{16}$ in both (VI) and (VIa) as defined hereinbefore;

(VII)

[structure VII with F substituents]

such that the corresponding spirolactone (VIIa) is as follows:

(VIIa)

[structure VIIa with F substituents]

with $R^{13}$, $R^{14}$, $R^{15}$ and $R^{16}$ in both (VII) and (VIIa) as defined hereinbefore;

(VIII)

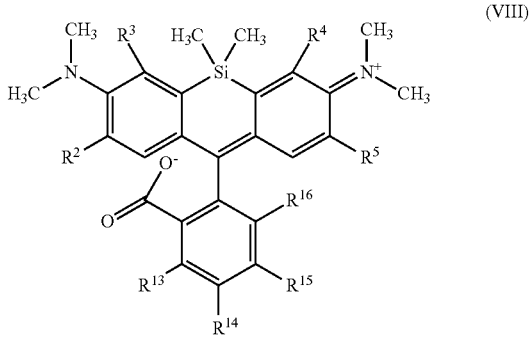

such that the corresponding spirolactone (VIIIa) is as follows:

(VIIIa)

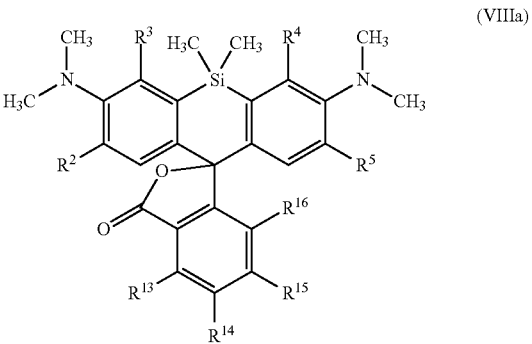

with $R^{13}$, $R^{14}$, $R^{15}$ and $R^{16}$ in both (VIII) and (VIIIa) as defined hereinbefore; and $R^2$, $R^3$, $R^4$ and $R^5$ being independently H, F, Cl, Br;

and alternative protonation stages of (VI), (VII) and (VIII), comprising negatively or positively charged counterions.

Even more specifically, currently preferred embodiments of the invention are:

(IX)

[structure IX]

(X)

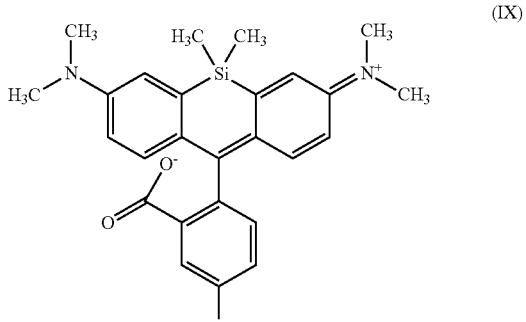

and alternative protonation stages of (IX) and (X), comprising negatively or positively charged counterions.

A further embodiment of the invention pertains to compounds as outlined hereinbefore, wherein at least one of $R^1$, $R^2$, $R^3$, $R^4$, $R^5$, $R^6$, $R^8$, $R^9$, $R^{10}$, $R^{11}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, preferably at least one of $R^{13}$, $R^{14}$ and $R^{15}$, is L-R*, and wherein each L independently is a covalent linkage, each or some of the L being the same or different;

each R* independently is chosen from the group consisting of acrylamide; an activated ester of a carboxylic acid; a hydroxyl; an anhydride of a carboxylic acid; an aldehyde; an alkyl halide; a sulfonate; an amine; an anhydride; an aniline; an aryl halide; an azide; an alkyne; a boronate; a carboxylic acid; a carbodiimide; a diazoalkane; an epoxide; a glycol; a haloacetamide; a halotriazine; a hydrazine; a hydroxylamine; an imido ester; an isocyanate; an isothiocyanate; a ketone; a maleimide; a phosporamidite; a sulfonyl halide; a thiol; an alkine; a phosphine; a sulfonyl ester —$CH_2OSO_2R$, wherein R is $C_6H_4CH_3$ (tosyl), $CH_3$ (mesyl), $CF_3$ (triflate) or $CF_2CF_3$ (nonaflate).

Due to the reactive groups being introduced by the -L-R* moiety, the compounds of the invention can thereby be modified such as to allow for reactivity towards certain targets. Introduction of such reactive groups into the compounds of the invention can be accomplished by routine procedures known to the person of skill in the art.

More specifically, currently preferred embodiments of compounds possessing such -L-R* moieties as outlined hereinbefore are:

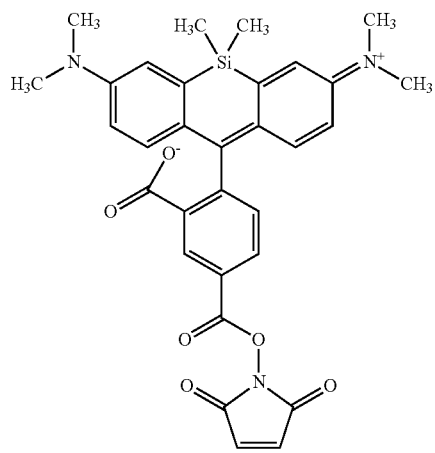

(XI)

or its corresponding spirolactone;

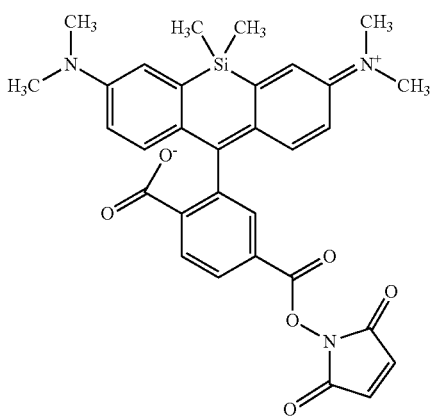

(XII)

or its corresponding spirolactone;

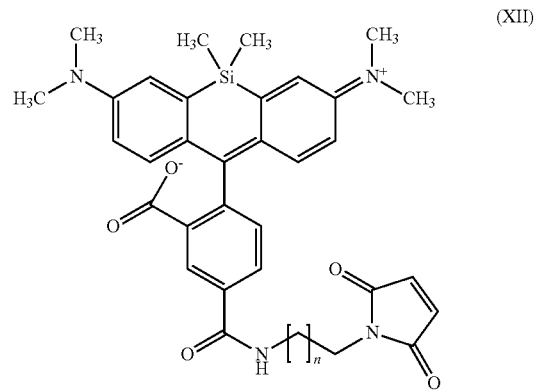

(XII)

or its corresponding spirolactone and with n=1-11;

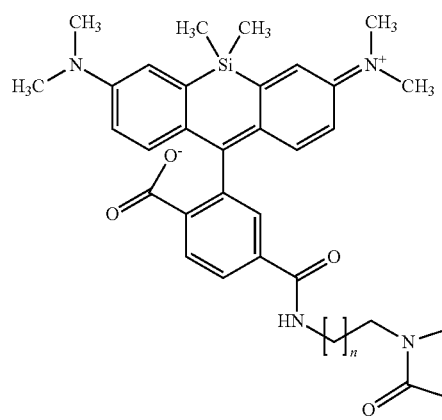

(XIV)

or its corresponding spirolactone and with n=1-11;

and alternative protonation stages of (XI), (XII), (XIII) and (XIV), comprising negatively or positively charged counterions.

Yet a further embodiment of the invention pertains to compounds as outlined hereinbefore, wherein at least one of $R^1$, $R^2$, $R^3$, $R^4$, $R^5$, $R^6$, $R^8$, $R^9$, $R^{10}$, $R^{11}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, preferably at least one of $R^{13}$, $R^{14}$ and $R^{15}$, is -L'-S, and wherein each L' independently is a covalent linkage, each or some the same or different;

each S independently is an amino acid; a peptide; a protein; a monosaccharide; a disaccharide; a polysaccharide; an ion-complexing group, preferably a calcium-complexing group; a lanthanide-complexing group; a nickel-complexing group; a cobalt-complexing group; ethylenediamine tetraacetic acid; nitrilotriacetic acid; a nucleotide; a substrate of an enzyme; an inhibitor of an enzyme, preferably an irreversible inhibitor of an enzyme forming a covalent bond with an enzyme; an agonist of a receptor; a ligand that binds with a KD of at least 10 µM to a nucleic acid; a ligand that binds with a KD of at least 10 µM to a protein; a substrate of SNAP-tag; a substrate of CLIP-tag; a substrate of Halotag, a ligand binding to dihydrofolate reductase; methotrexate; trimethoprim; a substrate of biotin ligase; a substrate of phosphopantetheine transferase; a substrate of lipoic acid ligase; biotin; a ligand binding to streptavidin, avidin or neutravidin; a cofactor of an enzyme; a hormone; a toxin; a fluorophore; a nucleic acid polymer; a hapten; an antigen; a drug; a lipid; a lipid assembly; a non-biological organic polymer; a polymeric microparticle; an animal cell a plant cell; a bacterium, a yeast; a virus; a protist.

More specifically, currently preferred embodiments of compounds possessing such -L'-S moieties as outlined hereinbefore are:

(XV)

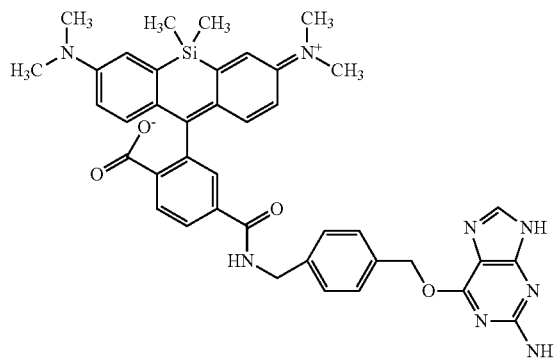

or its corresponding spirolactone;

(XVI)

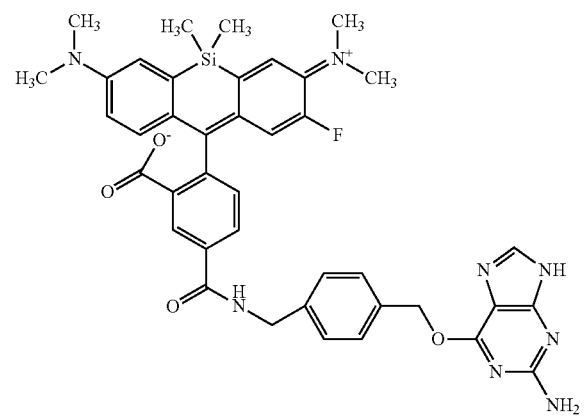

or its corresponding spirolactone;

(XVII)

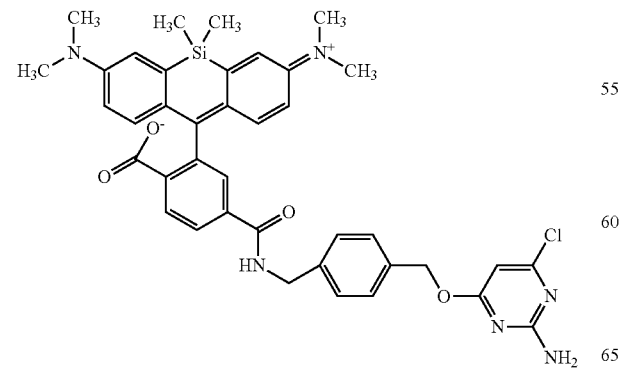

or its corresponding spirolactone;

(XVIII)

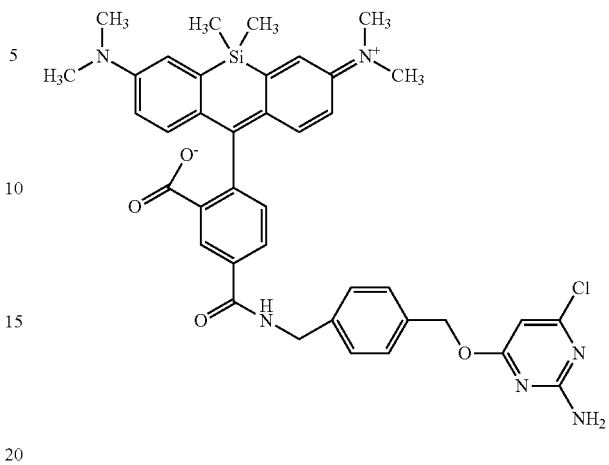

or its corresponding spirolactone;

(XIX)

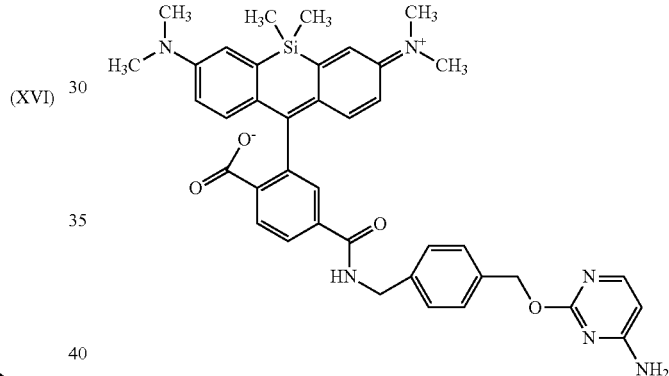

or its corresponding spirolactone;

(XX)

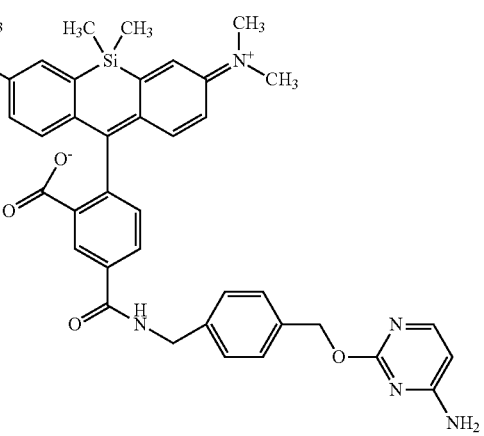

or its corresponding spirolactone;

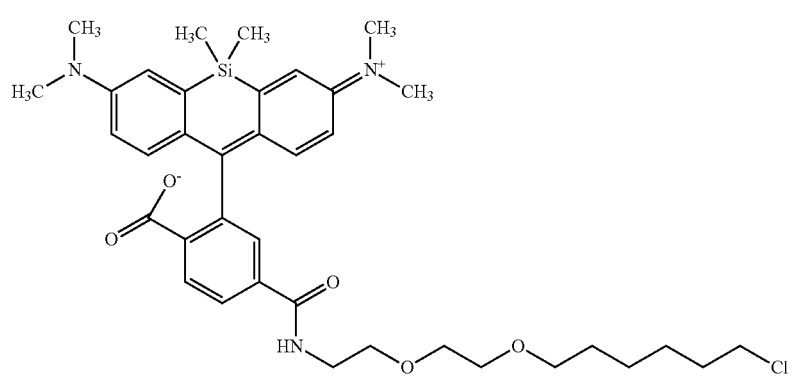

(XXI)

or its corresponding spirolactone;

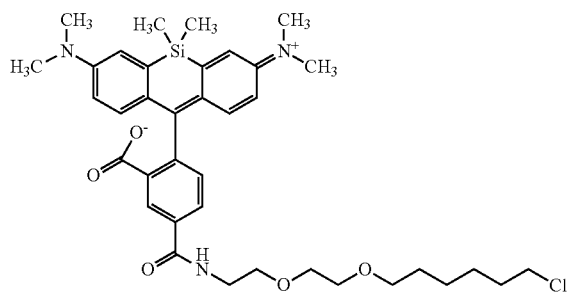

(XXII)

or its corresponding spirolactone;

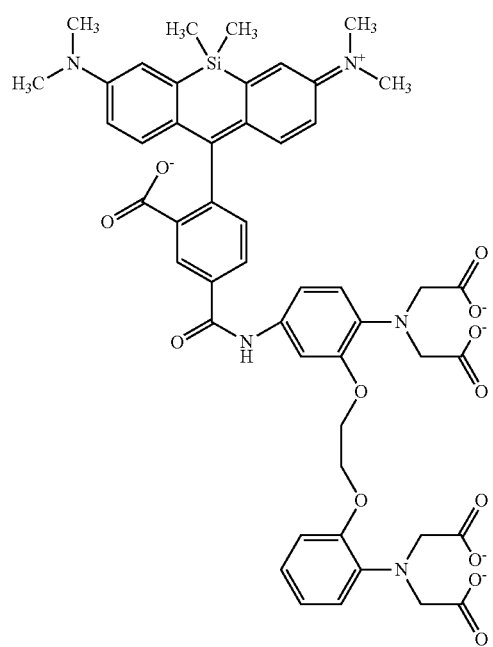

(XXIII)

or its corresponding spirolactone;

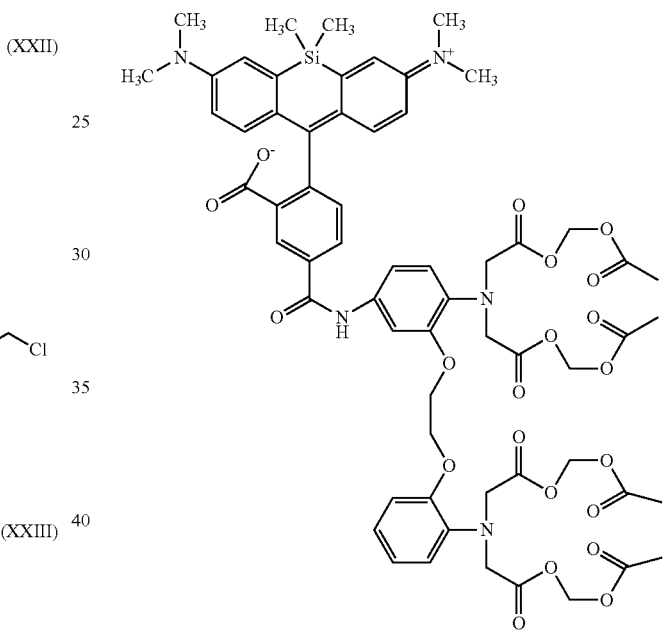

(XXIV)

or its corresponding spirolactone;
and alternative protonation stages of (XV), (XVI), (XVII), (XVIII), (XIX), (XX), (XXI), (XXII), (XXIII), (XXIV), comprising negatively or positively charged counterions.

It is being understood that currently preferably L and L' is/are independently a single covalent bond, or L and L' is/are a covalent linkage having 1-24 non-hydrogen atoms selected from the group consisting of C, N, O, P and S and is composed of any combination of single, double, triple or aromatic carbon-carbon bonds, carbon-nitrogen bonds, nitrogen-nitrogen bonds, carbon-oxygen bonds, carbon-sulfur bonds, phosphorous-oxygen bonds and phosphorous-nitrogen bonds.

A further aspect of the invention pertains to the use of the aforementioned compounds comprising a -L-R* moiety as outlined hereinbefore, in a reaction with a substrate molecule that binds or can preferably be enzymatically coupled to a specific target, in particular a protein or peptide, resulting in a compound comprising a -L'-S moiety as outlined hereinbefore, wherein the reaction occurs between the substrate molecule and the compound comprising a -L-R* moiety at least at one of $R^1$, $R^2$, $R^3$, $R^4$, $R^5$, $R^6$, $R^{13}$, $R^{14}$ and $R^{15}$, preferably at least one of $R^{13}$, $R^{14}$ and $R^{15}$, thereby establishing a binding moiety towards a specific target at least at one of $R^1$, $R^2$, $R^3$, $R^4$, $R^5$, $R^6$, $R^{13}$, $R^{14}$ and $R^{15}$, preferably at least one of $R^{13}$, $R^{14}$ and $R^{15}$.

More specifically, in the use as outlined above, the specific target, in particular the protein or peptide on the one hand and the binding moieties on the other hand are chosen from the group consisting of SNAP-tag and benzylguanine; CLIP-tag and benzylcytosine; HALO-tag and 1° chloride; dihydrofolate reductase; trimethoprim; kinase and kinase inhibitor; DNA polymerase and its substrate(s).

In accordance with currently preferred embodiments of the use as outlined above, the substrate can be enzymatically coupled to the target by an enzyme chosen from the group consisting of phosphopantetheine transferase, biotin ligase, liopoic acid ligase; DNA polymerase; DNA methyltransferase.

Yet a further aspect of the invention pertains to a method of providing a binding agent for a specific target, in particular a protein, peptide or nucleic acid, characterized in that a compound comprising an -L-R* moiety as outlined hereinbefore at least at one of $R^1$, $R^2$, $R^3$, $R^4$, $R^5$, $R^6$, $R^{13}$, $R^{14}$ and $R^{15}$, preferably at least one of $R^{13}$, $R^{14}$ and $R^{15}$ is reacted with a substrate molecule that binds or can preferably be enzymatically bound to said target.

Another aspect of the present invention is a kit-of-parts, comprising i) a compound as outlined hereinbefore;

ii) optionally, a second compound that is able to bind to a specific target, in particular a protein or peptide, and which second compound is able to react with a compound comprising a -L-R moiety as outlined hereinbefore at least at one of $R^1$, $R^2$, $R^3$, and $R^4$, preferably at least one of $R^2$ and $R3$;

iii) optionally, an activating agent to allow for the reaction of either i) or the reaction product of i) and ii) with the specific target to occur;

iv) optionally, instructions for use of the kit-of-parts in accordance with the various methods and uses outlined herein.

In especially preferred embodiments, the compound i) is able to bind to a specific target, in particular by means of a -L'-S moiety as outlined hereinbefore.

It is being understood that the compounds as outlined herein and the kit-of-parts is especially useful for the labelling of proteins or nucleic acids in vitro, in living cells or in living organisms. This will be readily apparent for the person of skill in the art, especially in view of the experimental details and applications outlined hereinafter.

In particular, the compounds and the kit-of-parts as outlined hereinbefore will prove useful in fluorescence spectroscopy; fluorescence microscopy; fluorescence imaging; stochastic optical reconstruction microscopy (STORM); direct STORM (dSTORM); ground state depletion microscopy followed by individual molecule return (GSDIM); ground state depletion (GSD) microscopy; single-molecule spectroscopy; Förster resonance energy transfer (FRET) applications, in particular time-resolved; fluorescence correlation spectroscopy; fluorescence anisotropy spectroscopy; correlative fluorescence-electron microscopy; fluorescence activated cell sorting; oxygen, fluoride or glycerol sensing in vitro, in living cells or living organisms.

Experimental Details

The invention will be described below by means of embodiments and experiments; it is to be understood that this is not intended to limit the subject-matter of the invention in any way.

A. Synthesis

All chemical reagents and dry solvents for synthesis were purchased from commercial suppliers (Sigma-Aldrich, Fluka, Acros) and were used without further purification or distillation. The composition of mixed solvents is given by the volume ratio (v/v). Thin layer chromatography (TLC) was performed on TLC-aluminum sheets (Silica gel 60 $F_{254}$). Flash column chromatography was performed with Merck silica gel (230-400 mesh). $^1H$ and $^{13}C$ nuclear magnetic resonance (NMR) spectra were recorded on a Bruker DPX 400 (400 MHz for $^1H$, 100 MHz for $^{13}C$, respectively) or Bruker 500 (500 MHz for $^1H$, 125 MHz for $^{13}C$, respectively), with chemical shifts (δ) reported in ppm relative to the solvent residual signals of $CDCl_3$ (7.16 ppm for $^1H$, 77.16 ppm for $^{13}C$), $CD_3OD$ (3.31 ppm for $^1H$, 49.00 ppm for $^{13}C$), DMSO-$d_6$ (2.50 ppm for $^1H$, 39.52 ppm for $^{13}C$), acetone-$d_6$ (2.05 ppm for $^1H$, 29.84 ppm for $^{13}C$), and coupling constants reported in Hz. High resolution mass spectra (HRMS) were measured on a Micromass Q-TOf Ultima spectrometer with electron spray ionization (ESI). Reversed phase analytical HPLC was run on a Waters 2790 separation module and products were detected at 280 nm using a 2487 dual λ absorption detector. The standard gradient that was used for the purifications was: starting at water including 0.1% TFA for 2 minutes and raising to 100% acetonitrile within 17 minutes. A 3.9×300 mm Prep Nova-Pak HR C18 6 μm column from Waters was used to determine the purity of the products. Preparative HPLC was performed on a Waters 600 controller and with a Waters 2487 dual λ absorption detector using a SunFire™ Prep C18 OBD™ 5 μm 19×150 mm Column.

The general outline of the synthesis is as follows (for more details cf Sections A.1 to A.12, below):

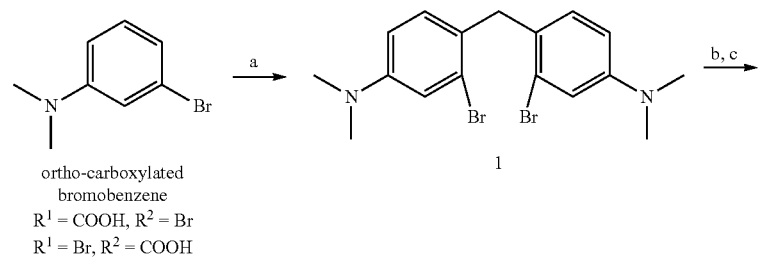

ortho-carboxylated
bromobenzene
$R^1 = COOH$, $R^2 = Br$
$R^1 = Br$, $R^2 = COOH$

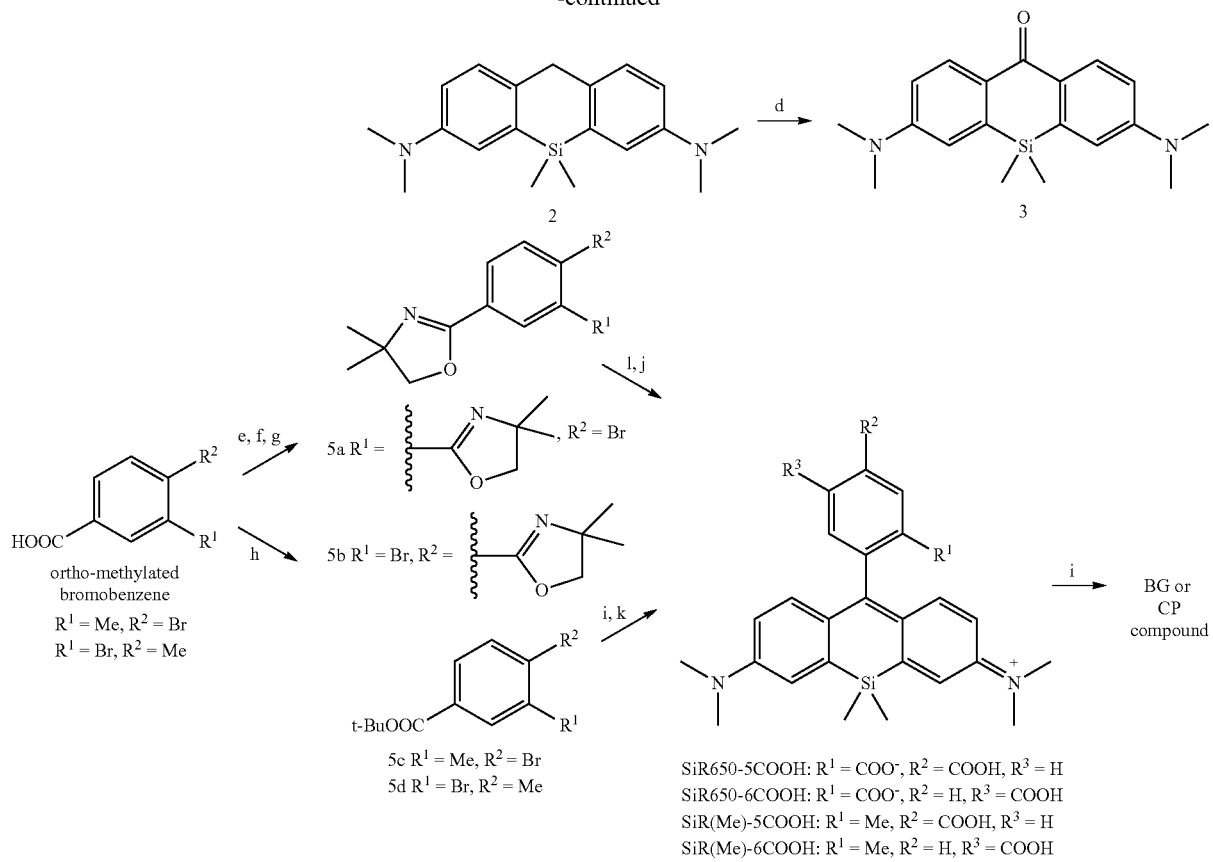

Reaction and condition: (a) HCHO, AcOH, 70° C., 30 min.; (b) sec-BuLi, THF, -78° C.; (c) Me₂SiCl₂, -78° C. to rt.;
(d) KMnO₄, acetone, -15° C.; (e) SOCl₂, cat. DMF, reflux, 2-3 hr.; (f) 2-amino-2-methylpropan-1-ol, DIEA, CH₂Cl₂, 0° C. to rt., 2 hr-overnight;
(g) SOCl₂, rt., 1-3 hr.; (h) (Boc)₂O, DMAP, THF, reflux, overnight;
(i) tert-BuLi, THF, -78° C., then 3, -78° C. to rt.; (j) 6N HCl aq. 80° C., overnight; (k) 6N HCl, 40° C., 1 hr.; (l) BG—NH₂ or CP—NH₂, PyBOP, DIEA, DMSO, rt., 2-4 hr.

A.1 4,4'-methylenebis(3-bromo-N,N-dimethylaniline) (1)

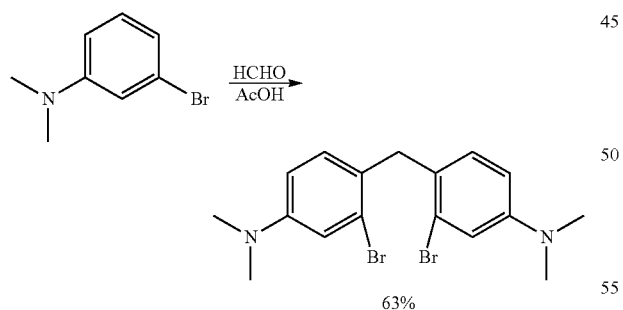

63%

3-Bromo-N,N-dimethylaniline (5.00 g, 25 mmol, 2 eq.) was dissolved in 37% formaldehyde solution (5 ml) and acetic acid (40 ml), and stirred at 60° C. for 30 minutes. After cooling, acetic acid was evaporated, then saturated NaHCO₃ aqueous solution was added carefully. The aqueous phase was extracted with ethyl acetate twice, and the combined organic phase was washed with water and brine, dried over Na₂SO₄, then filtered and evaporated. The resulting residue was purified by silica gel column chromatography (n-hexane/EtOAc=90/10) to obtain 4,4'-methylenebis(3-bromo-N,N-dimethylaniline) 1 as a white solid. (3.24 g, 63%)

$^{s1}$H NMR (400 MHz, CDCl₃) δ 6.94 (d, 2H, J=2.7 Hz), 6.85 (d, 2H, J=8.6 Hz), 6.59 (dd, 2H, J=8.6, 2.6 Hz), 4.00 (s, 2H), 2.92 (s, 12H).

$^{13}$C NMR (100 MHz, CDCl₃) δ 150.2, 130.9, 127.2, 125.7, 116.4, 112.0, 40.7, 40.0. HRMS (ESI): m/z calc. for C₁₇H₂₀Br₂N₂ 411.0071, 413.0052; found 411.0092 (5.21 ppm), 413.0056 (0.97 ppm) [M+H]⁺.

A.2 3,7-Bis(dimethylamino)-5,5-dimethyldibenzo[b,e]silin-10(5H)-one (3)

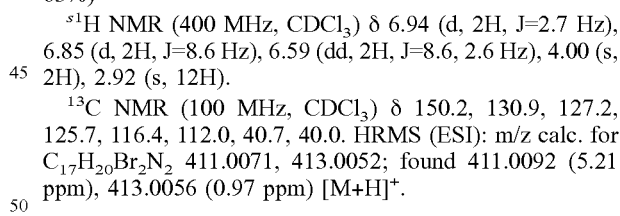

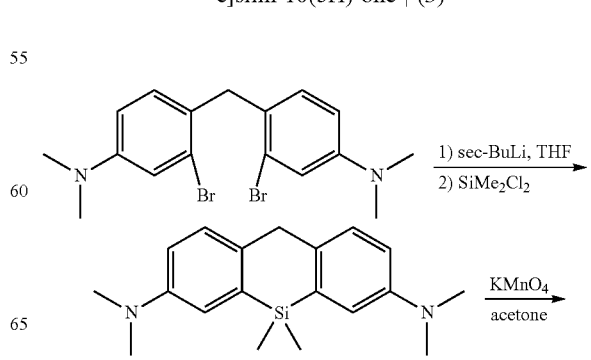

-continued

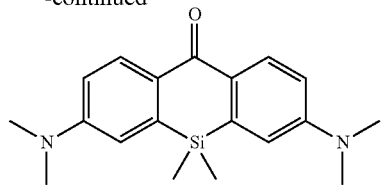

4,4'-Methylenebis(3-bromo-N,N-dimethylaniline 1 (2.00 g, 4.85 mmol, 1 eq.) was dissolved in dry THF (200 ml) and stirred at −78° C. on the $CO_2(s)$/acetone bath. sec-BuLi (1.4 mol/l solution in n-hexane, 10 ml, 14.0 mmol, 3 eq.) was slowly added for 30 minutes to the solution and stirred for further 2 hr at the same temperature. $SiMe_2Cl_2$ (1 ml, 8.22 mmol, 1.8 eq.) was added to the reaction mixture and stirred at room temperature for 2 hr. 1N HCl aqueous solution was added carefully to neutralize the solution, and THF was evaporated. The resulting aqueous solution was extracted with EtOAc, and the organic phase was washed with saturated $NaHCO_3$ aqueous solution, water and brine, dried over $Na_2SO_4$, filtered and evaporated to obtain the crude including $N^3,N^3,N^7,N^7,5,5$-hexamethyl-5,10-dihydrodibenzo[b,e]siline-3,7-diamine 2, which was used for the next reaction immediately due to its high sensitivity toward oxygen. The resulting crude including 2 was dissolved in acetone (30 ml) and stirred at −15° C. on the crashed ice/NaCl(s) bath. $KMnO_4$ powder was added portionwise (300 mg×6) for 30 minutes, and stirring was continued for further 2 hr at the same temperature. The purple suspension was filtered through a Celite pad, and the yellow filterate was evaporated. The resulting residue was purified by silica gel column chromatography (n-hexane/$CH_2Cl_2$=20/80) to obtain 3,7-Bis(dimethylamino)-5,5-dimethyldibenzo[b,e]silin-10(5H)-one as a yellow solid. (689 mg, 41%)

$^1$H NMR (400 MHz, $CDCl_3$) δ 8.44 (d, 2H, J=8.9 Hz), 6.87 (dd, 2H, J=9.0 Hz, 2.4 Hz), 6.83 (d, 2H, J=2.4 Hz), 3.12 (s, 12H), 0.51 (s, 6H).

$^{13}$C NMR (100 MHz, $CDCl_3$) δ 185.4, 151.5, 140.6, 131.7, 129.7, 114.4, 113.2, 40.2, −0.8.

HRMS (ESI): m/z calc. for $C_{19}H_{24}N_2OSi$ 325.1736; found 325.1730 (−1.85 ppm), [M+H]$^+$.

A.3 4-bromo-$N^1,N^3$-bis(1-hydroxy-2-methylpropan-2-yl)isophthalamide | (4a)

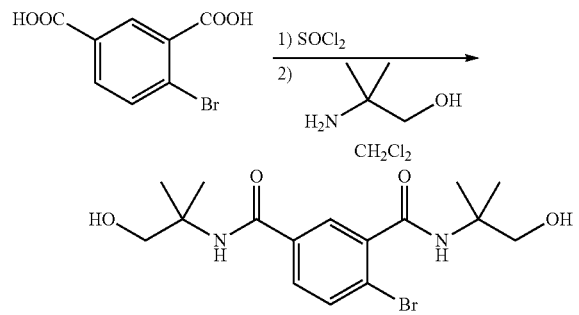

4-bromo-$N^1,N^3$-bis(1-hydroxy-2-methylpropan-2-yl)isophthalamide

2-Bromoisophthalic acid (1.50 mg, 6.12 mmol, 1 eq.) was suspended into $SOCl_2$ (10 ml) in the presence of DMF (1 drop), and the solution was refluxed for 2 hr. After cooling to room temperature and evaporating $SOCl_2$ and dried in vacuo, the resulting compound was dissolved in $CH_2Cl_2$ (30 ml), and was dropped into a solution of 2-amino-2-methyl-propan-1-ol (1.10 g, 12.3 mmol, 2 eq.) and DIEA (2 ml) in $CH_2Cl_2$ (30 ml), and the solution stirred at room temperature overnight. Saturated $NaHCO_3$ aqueous solution was added to the reaction mixture and extracted with EtOAc (×3), and the combined organic phase was washed with water and brine, dried over $Na_2SO_4$, filtered and evaporated to obtain 4-bromo-$N^1,N^3$-bis(1-hydroxy-2-methylpropan-2-yl)isophthalamide 4a as a white solid. (2.09 g, 97%)

$^1$H NMR (400 MHz, DMSO-$d_6$) δ 7.87 (s, 1H), 7.78 (d, 1H, J=2.1 Hz), 7.71 (m, 3H), 4.88 (t, 1H, J=6.0 Hz), 4.82 (t, 1H, J=6.1 Hz), 3.51 (d, 2H, J=5.9 Hz), 3.50 (d, 2H, J=5.9 Hz), 1.31 (s, 6H), 1.30 (s, 6H).

$^{13}$C NMR (100 MHz, DMSO-$d_6$) δ 167.2, 165.5, 140.0, 135.0, 132.7, 129.6, 127.8, 122.1, 67.9, 67.6, 55.8, 55.7, 24.0, 23.9.

HRMS (ESI): m/z calc. for $C_{16}H_{23}BrN_2O_4$ 387.0919; found 387.0911 (−2.07 ppm), [M+H]$^+$.

A.4 2,2'-(4-bromo-1,3-phenylene)bis(4,4-di methyl-4,5-di hydrooxazole) | (5a)

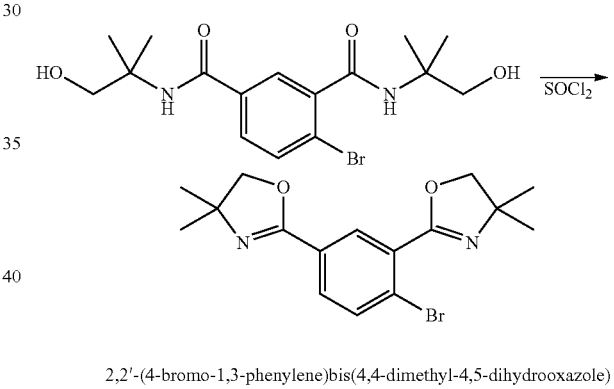

2,2'-(4-bromo-1,3-phenylene)bis(4,4-dimethyl-4,5-dihydrooxazole)

2-Bromo-$N^1,N^3$-bis(1-hydroxy-2-methylpropan-2-yl) isophthalamide (900 mg, 2.32 mmol) was dissolved in $SOCl_2$ (5 ml) and stirred at room temperature for 1 hr. After evaporating $SOCl_2$, saturated $NaHCO_3$ aqueous solution was added carefully to neutralize the solution. The resulting water phase was extract with EtOAc (×2), and the combined organic phase was washed with water and brine, dried over $Na_2SO_4$, filtered and evaporated. The resulting residue was purified by silica gel column chromatography ($CH_2Cl_2$/MeOH=95/5) to obtain 2,2'-(4-bromo-1,3-phenylene)bis(4,4-dimethyl-4,5-dihydrooxazole) 5a as a colorless liquid. (772 mg, 94%)

$^1$H NMR (400 MHz, $CDCl_3$) δ 8.21 (d, 1H, J=2.1 Hz), 7.82 (dd, 1H, J=8.4, 2.1 Hz), 7.67 (d, 1H, J=8.4 Hz), 4.14 (s, 2H), 4.12 (s, 2H), 1.42 (s, 6H), 1.38 (s, 6H). $^{13}$C NMR (100 MHz, $CDCl_3$) δ 160.9, 160.7, 133.7, 130.9, 130.8, 130.6, 127.3, 125.0, 79.5, 79.4, 68.4, 67.9, 28.4, 28.3.

HRMS (ESI): m/z calc. for $C_{16}H_{19}BrN_2O_2$ 351.0708; found 351.0704 (−1.14 ppm), [M+H]$^+$.

A.5 2-bromo-$N^1,N^4$-bis(1-hydroxy-2-methylpropan-2-yl)terephthalamide (4b)

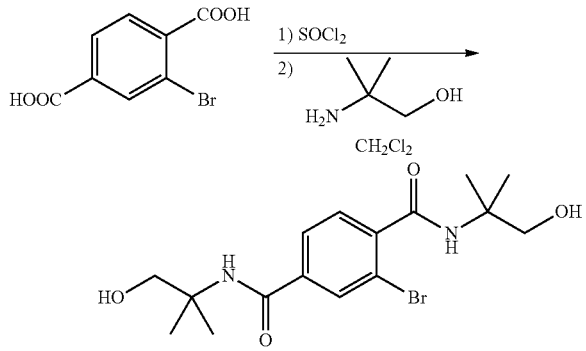

2-Bromoterephthalic acid (750 mg, 3.06 mmol, 1 eq.) was suspended into SOCl$_2$ (5 ml) in the presence of DMF (1 drop), and the solution was refluxed for 3 hr. After cooling to room temperature, evaporating and dried in vacuo, the resulting compound was dissolved in CH$_2$Cl$_2$ (10 ml), and was dropped into a solution of 2-amino-2-methylpropan-1-ol (750 mg, 8.41 mmol, 2.7 eq.) and DIEA (1.5 ml) in CH$_2$Cl$_2$ (10 ml), and the solution was stirred at room temperature overnight. Saturated NaHCO$_3$ aqueous solution was added to the reaction mixture and extracted with EtOAc (×3), and combined organic phase was washed with water and brine, dried over Na$_2$SO$_4$, filtered and evaporated to obtain 2-bromo-$N^1,N^4$-bis(1-hydroxy-2-methylpropan-2-yl)terephthalamide 4b as a white solid. (922 mg, 78%)

$^1$H NMR (400 MHz, DMSO-d$_6$) δ 8.04 (d, 1H, J=1.5 Hz), 7.86 (bs, 1H), 7.82 (dd, 1H, J=7.9, 1.7 Hz), 7.72 (bs, 1H), 7.43 (d, 1H, J=7.9 Hz), 4.87 (t, 1H, J=6.1 Hz), 4.82 (t, 1H, J=6.1 Hz), 3.51 (d, 2H, J=6.2 Hz), 3.50 (d, 2H, J=6.2 Hz), 1.31 (s, 6H), 1.30 (s, 6H).

$^{13}$C NMR (100 MHz, DMSO-d$_6$) δ 167.2, 164.9, 142.3, 137.7, 131.6, 128.8, 126.9, 119.1, 67.8, 67.5, 55.8, 24.0, 23.9.

HRMS (ESI): m/z calc. for C$_{16}$H$_{23}$BrN$_2$O$_4$ 387.0919; found 389.0915 (−1.03 ppm), [M+H]$^+$.

A.6 2,2'-(2-bromo-1,4-phenylene)bis(4,4-dimethyl-4,5-dihydrooxazole) (5b)

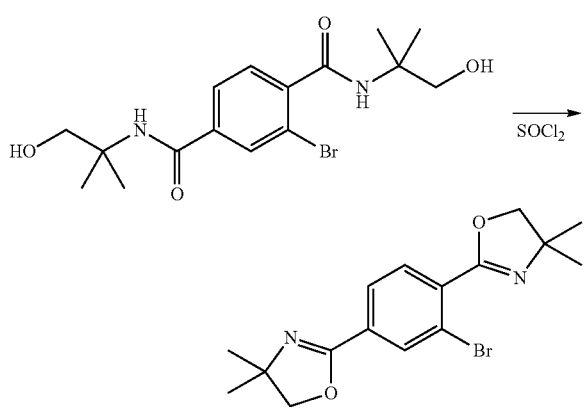

2-Bromo-$N^1,N^4$-bis(1-hydroxy-2-methylpropan-2-yl)terephthalamide (880 mg, 2.27 mmol) was dissolved in SOCl$_2$ (4 ml) and stirred at room temperature for 90 minutes. After evaporating SOCl$_2$, saturated NaHCO$_3$ aqueous solution was added carefully to neutralize the solution. The resulting water phase was extract with EtOAc (×2), and the combined organic phase was washed with water and brine, dried over Na$_2$SO$_4$, filtered and evaporated. The resulting residue was purified by silica gel column chromatography (EtOAc/CH$_2$Cl$_2$=50/50 to 100/0) to obtain 2,2'-(2-bromo-1,4-phenylene)bis(4,4-dimethyl-4,5-dihydrooxazole) 5b as a white solid. (578 mg, 73%)

$^1$H NMR (400 MHz, DMSO-d$_6$) δ 8.08 (d, 1H, J=1.5 Hz), 7.91 (dd, 1H, J=8.1, 1.7 Hz), 7.77 (d, 1H, J=8.0 Hz), 4.16 (s, 2H), 4.13 (s, 2H), 1.32 (s, 6H), 1.30 (s, 6H).

$^{13}$C NMR (100 MHz, DMSO-d$_6$) δ 160.0, 159.3, 132.7, 132.6, 132.1, 131.3, 127.3, 121.4, 79.3, 79.1, 68.7, 68.3, 28.6, 28.4.

HRMS (ESI): m/z calc. for C$_{16}$H$_{19}$BrN$_2$O$_2$ 351.0708; found 351.0719 (3.13 ppm), [M+H]$^+$.

A.7 tert-butyl 4-bromo-3-methylbenzoate (5c)

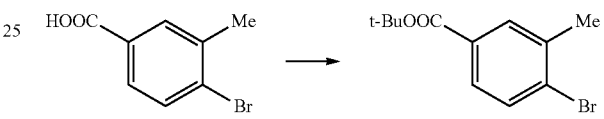

4-Bromo-3-methylbenzoic acid (740 mg, 3.44 mmol, 1 eq.), (Boc)$_2$O (1.92 g, 8.78 mmol, 2.5 eq.) and DMAP (93 mg, 0.764 mmol, 1 eq.) were dissolved in dry THF (10 ml) and refluxed overnight. After cooling to room temperature and evaporating the solvent, the residue was dissolved in Et$_2$O and washed with saturated NaHCO$_3$ aqueous solution, water and brine, dried over Na$_2$SO$_4$, filtered and evaporated. The resulting crude was purified by silica gel column chromatography (n-hexane/EtOAc=95/5) to obtain tert-butyl 4-bromo-3-methylbenzoate as a pale yellow liquid. (647 mg, 87%)

$^1$H NMR (400 MHz, CDCl$_3$) δ 7.83 (d, 1H, J=1.7 Hz), 7.64 (dd, 1H, J=8.9, 1.6 Hz), 7.56 (d, 1H, J=8.8 Hz), 2.43 (s, 3H), 1.59 (s, 9H).

$^{13}$C NMR (100 MHz, CDCl$_3$) δ 165.3, 138.0, 132.3, 131.6, 131.1, 129.8, 128.2, 81.4, 28.2, 22.9.

A.8 tert-butyl 3-bromo-4-methylbenzoate (5d)

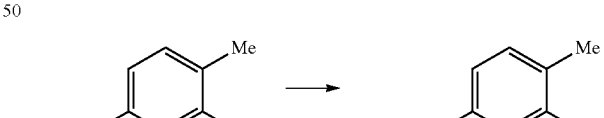

3-Bromo-4-methylbenzoic acid (1.40 g, 6.51 mmol, 1 eq.), (Boc)$_2$O (3.62 g, 16.6 mmol, 2.5 eq.) and DMAP (180 mg, 1.47 mmol, 0.2 eq.) were dissolved in dry THF (20 ml) and refluxed overnight. After cooling to room temperature and evaporating the solvent, the residue was dissolved in Et$_2$O and washed with saturated NaHCO$_3$ aqueous solution, water and brine, dried over Na$_2$SO$_4$, filtered and evaporated. The resulting crude was purified by silica gel column chromatography (n-hexane/EtOAc=95/5) to obtain tert-butyl 3-bromo-4-methylbenzoate 5d as a colorless liquid. (951 mg, 54%)

¹H NMR (400 MHz, CDCl₃) δ 8.15 (d, 1H, J=1.6 Hz), 7.83 (dd, 1H, J=7.9, 1.6 Hz), 7.29 (d, 1H, J=7.9 Hz), 2.46 (s, 3H), 1.61 (s, 9H).

¹³C NMR (100 MHz, CDCl₃) δ 164.5, 142.7, 133.3, 131.4, 130.5, 128.2, 124.6, 81.4, 28.2, 23.2.

A.9 SiR650-5COOH

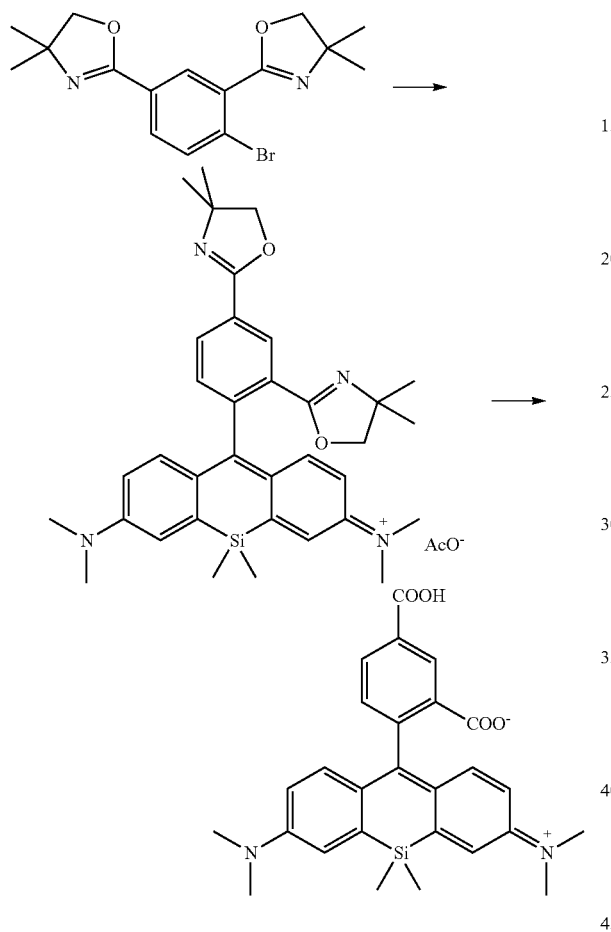

In an argon-flushed flask fitted with a septum cap, 5a (450 mg, 1.28 mmol, 2 eq.) was dissolved in dry THF (5 ml) and cooled at −78° C. on the CO₂(s)/acetone bath. tert-BuLi (800 μl, 1.28 mmol, 2 eq.) was dropped slowly and the solution was stirred at the same temperature for 1 hr. Compound 3 (188 mg, 0.581 mmol, 1 eq.) in dry THF (10 ml) was dropped via syringe at −78° C., and the solution was warmed to room temperature and stirred for 2 hr. Acetic acid (1 ml) was added to the reaction mixture on ice, the resulting intense blue solution was evaporated and lyophilized to obtain compound 6a as a blue solid, which was used for the next reaction without further purification. Compound 6a was dissolved in 6N HCl aq. (8 ml) and stirred at 80° C. overnight. After cooling to room temperature, the solution was added to saturated NaHCO₃ aqueous solution to adjust the pH to 1-2, and extracted with CH₂Cl₂ (×3), and the combined organic phase was washed with 0.1 N HCl (×2) and brine, dried over Na₂SO₄, filtered and evaporated. The resulting crude was purified with silica gel column chromatography (CH₂Cl₂/MeOH=90/10) to obtain SiR650-6COOH as a blue solid. (89.0 mg, 35%)

¹H NMR (400 MHz, CD₃OD) δ 8.53 (s, 1H), 8.36 (d, 1H, J=7.8 Hz), 7.33 (d, 1H, J=8.0 Hz), 7.06 (d, 2H, J=2.6 Hz), 6.73 (d, J=9.0 Hz, 2H), 6.66 (dd, J=9.0 Hz, 3.0 Hz, 2H), 2.98 (s, 12H), 0.66 (s, 3H), 0.57 (s, 3H).

¹³C NMR (100 MHz, CD₃OD) δ 172.0, 171.4, 159.4, 156.4, 149.7, 136.5, 135.1, 131.3, 127.8, 126.3, 125.9, 123.8, 116.5, 113.4, 39.1, −1.0, −2.8.

HRMS (ESI): m/z calc. for $C_{27}H_{29}N_2O_4Si$ 473.1897; found 473.1892 (−1.06 ppm), [M+H]⁺.

A.10 SiR650-6COOH

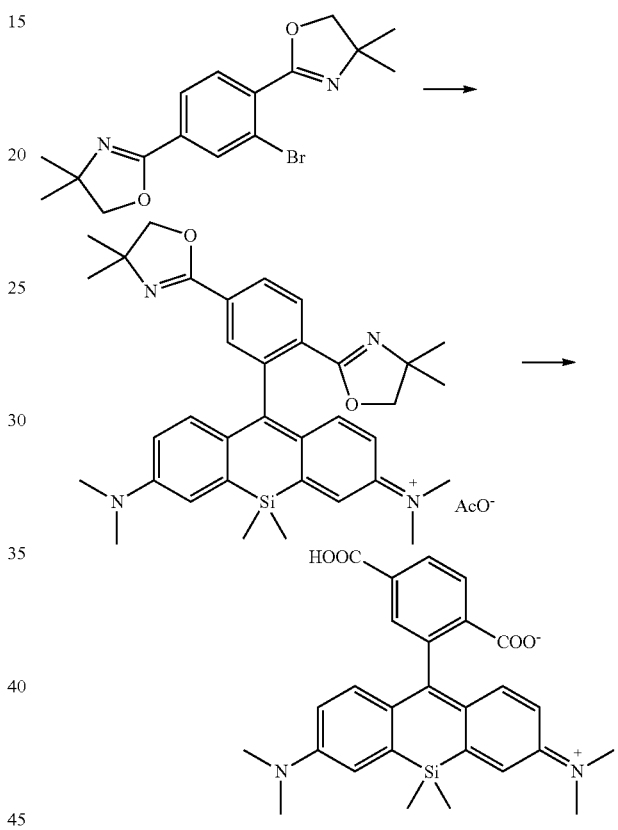

In an argon-flushed flask fitted with a septum cap, 5b (150 mg, 0.427 mmol, 2 eq.) was dissolved in dry THF (5 ml) and cooled at −78° C. on the CO₂(s)/acetone bath. tert-BuLi (300 μl, 0.481 mmol, 2 eq.) was dropped slowly and the solution was stirred at the same temperature for 1 hr. Compound 3 (69.0 mg, 0.214 mmol, 1 eq.) in dry THF (5 ml) was dropped via syringe at −78° C., and the solution was warmed to room temperature and stirred for 2 hr. Acetic acid (1 ml) was added to the reaction mixture on ice, the resulting intense blue solution was evaporated and lyophilized to obtain a blue solid, which was used for the next reaction without further purification. The intermediate was dissolved in 6N HCl aq. (12 ml) and stirred at 80° C. overnight. After cooling to room temperature, the solution was added to saturated NaHCO₃ aqueous solution (50 ml) to adjust the pH (1-2), and extracted with CH₂Cl₂ (×3), and the combined organic phase was washed with 0.1N HCl (×2) and brine, dried over Na₂SO₄, filtered and evaporated. The resulting crude was purified with silica gel column chromatography (CH₂Cl₂/MeOH=90/10) to obtain SiR650-6COOH as a blue solid. (79.2 mg, 86%)

¹H NMR (400 MHz, CD₃OD) δ 8.25 (dd, 1H, J=8.0, 1.1 Hz), 8.05 (d, 1H, J=8.0 Hz), 7.86 (d, 1H, J=1.0 Hz), 7.08 (d, 2H, J=2.8 Hz), 6.77 (d, 2H, J=9.2 Hz), 6.68 (dd, 2H, J=9.0, 2.9 Hz), 3.00 (s, 12H), 0.68 (s, 3H), 0.58 (s, 3H).
¹³C NMR (125 MHz, CD₃OD) δ 172.0, 171.6, 154.6, 149.8, 144.1, 136.7, 131.4, 129.6, 127.8, 127.3, 124.9, 124.4, 116.6, 113.5, 39.2, −0.9, −2.7.

HRMS (ESI): m/z calc. for $C_{27}H_{29}N_2O_4Si$ 473.1897; found 473.1898 (0.21 ppm), [M+H]⁺.

A.11 SiRMe-5COOH (Comparative Example)

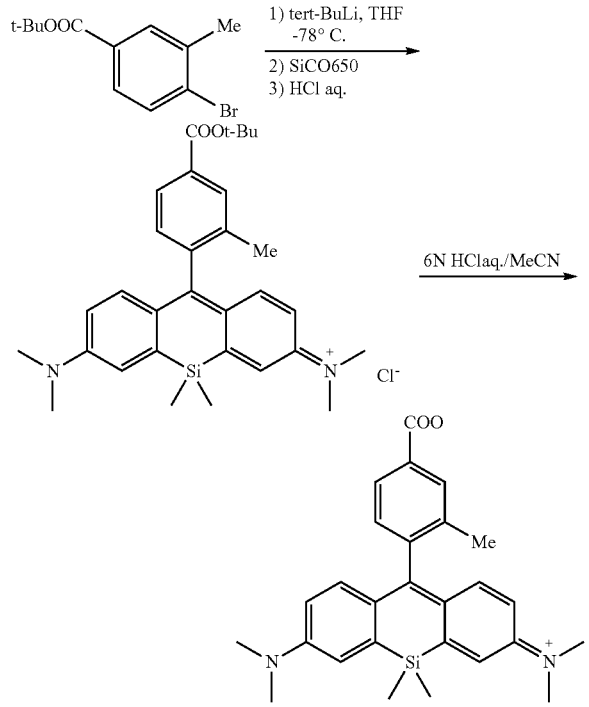

In an argon-flushed flask fitted with a septum cap, 5c (100 mg, 0.369 mmol, 4 eq.) was dissolved in dry THF (3 ml) and cooled at −78° C. on the CO₂(s)/acetone bath. tert-BuLi (250 μl, 0.401 mmol, 4 eq.) was dropped slowly and stirred at the same temperature for 1 hr. Compound 3 (25.2 mg, 0.077 mmol, 1 eq.) in dry THF (2 ml) was dropped via syringe at −78° C., and warmed to room temperature and stirred overnight. 0.1N HClaq. was added to the reaction mixture, and the resulting intense blue solution was basified with saturated NaHCO₃ aqueous solution, and extracted with CH₂Cl₂ (×2). The combined organic phase was washed with brine, dried over Na₂SO₄, filtered and evaporated to obtain a blue solid, which was used for the next reaction without further purification. The intermediate was dissolved in 6N HCl aq. (8 ml) and MeCN (2 ml) and stirred at 40° C. for 1 hr. After cooling to room temperature, the solution was added to 0.1N NaOHaq. to adjust the pH to 2-3, and extracted with CH₂Cl₂ (×2), and the combined organic phase was washed with brine, dried over Na₂SO₄, filtered and evaporated. The crude was purified with silica gel column chromatography (CH₂Cl₂/MeOH=90/10) to obtain SiRMe-5COOH as a blue solid. (27.5 mg, 88%)

¹H NMR (400 MHz, CD₃OD) δ 8.09 (s, 1H), 8.05 (dd, 1H, J=7.9, 1.2 Hz), 7.40 (d, 2H, J=2.8 Hz), 7.28 (d, 1H, J=7.9 Hz), 7.05 (d, 2H, J=9.7 Hz), 6.81 (dd, 2H, J=9.7, 2.8 Hz), 3.37 (s, 12H), 2.12 (s, 3H), 0.64 (s, 3H), 0.63 (s, 3H).
¹³C NMR (100 MHz, CD₃OD) δ 167.8, 154.5, 148.1, 143.5, 140.5, 136.3, 131.2, 131.1, 129.2, 126.7, 126.6, 121.0, 114.0, 39.5, 18.0, −2.5, −2.7.

HRMS (ESI): m/z calc. for $C_{27}H_{31}N_2O_2Si$ 443.2155; found 443.2170 (3.40 ppm), [M+H]⁺.

A.12 SiRMe-6COOH (Comparative Example)

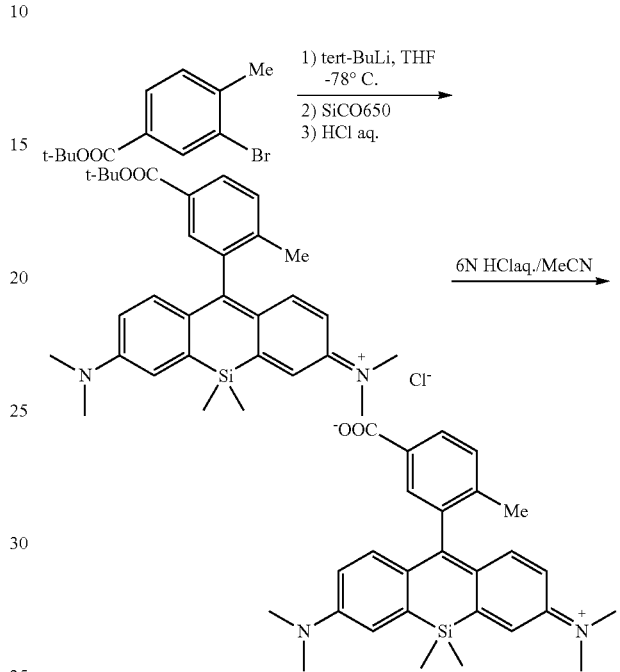

In an argon-flushed flask fitted with a septum cap, 5d (100 mg, 0.369 mmol, 4 eq.) was dissolved in dry THF (3 ml) and cooled at −78° C. on the CO₂(s)/acetone bath. tert-BuLi (250 μl, 0.401 mmol, 4 eq.) was dropped slowly and stirred at the same temperature for 1 hr. Compound 3 (24.0 mg, 0.074 mmol, 1 eq.) in dry THF (2 ml) was dropped via syringe at −78° C., and warmed to room temperature and stirred for 2 hr. 0.1N HClaq. was added to the reaction mixture, and the resulting intense blue solution was basified with saturated NaHCO₃ aqueous solution, and extracted with CH₂Cl₂ (×3). The combined organic phase was washed with brine, dried over Na₂SO₄, filtered and evaporated to obtain a blue solid, which was used for the next reaction without further purification. The intermediate was dissolved in 6N HCl aq. (8 ml) and MeCN (2 ml) and stirred at 40° C. for 1 hr. After cooling to room temperature, the solution was added to 0.1N NaOHaq. to adjust the pH to 2-3, and extracted with CH₂Cl₂ (×2), and the combined organic phase was washed with brine, dried over Na₂SO₄, filtered and evaporated. The crude was purified with silica gel column chromatography (CH₂Cl₂/MeOH=90/10) to obtain SiRMe-6COOH as a blue solid. (23 mg, 80%)

¹H NMR (400 MHz, CD₃OD) δ 8.12 (d, 1H, J=7.3 Hz), 7.77 (s, 1H), 7.49 (d, 1H, J=7.6 Hz), 7.39 (s, 2H), 7.07 (d, 2H, J=9.5 Hz), 6.78 (d, 2H, J=9.6 Hz), 3.37 (s, 12H), 2.10 (s, 3H), 0.65 (s, 3H), 0.63 (s, 3H).
¹³C NMR (100 MHz, DMSO-d₆) δ 167.3, 158.4, 158.1, 154.2, 147.7, 140.4, 138.6, 130.4, 130.0, 126.8, 122.0, 119.3, 116.3, 115.1, 41.0, 19.4, −0.6, −0.9.

HRMS (ESI): m/z calcd for $C_{27}H_{31}N_2O_2Si$ 443.2155; found 443.2162 (1.58 ppm), [M+H]⁺.

B. Synthesis of BG- or CP-fluorophores

O$^6$-(4-Aminomethyl)benzylguanine (BG-NH2) and 4-(4-aminomethyl)benzyloxy-6-chloropyrimidin-2-amine (CP-NH2) were prepared according to the previously reported procedures (Keppler et al., Methods 2004, 32, 437; Srikun et al., C. J. J. Am. Chem. Soc. 2010, 132, 4455), respectively.

SiR dyes (5.0 mg, 1 eq.), BG-NH$_2$ (6.5 mg 2.4 eq.) or CP—NH$_2$ (6.4 mg, 2.4 eq.), PyBOP (12.0 mg, 2.4 eq.) were dissolved in dry DMSO (500 μl) in the presence of DIEA (10 μl), and the solution was stirred at room temperature for 1-3 hr. The reaction mixture was purified by HPLC to obtain the desired BG- or CP-SiR conjugates.

B.1 SiR650-5BG (5.3 mg, 69%)

$^1$H NMR (400 MHz, CD$_3$OD) δ 9.40 (t, 1H, J=5.9 Hz), 8.71 (d, 1H, J=1.5 Hz), 8.35 (s, 1H), 8.24 (dd, 1H, J=8.0, 1.6 Hz), 7.59 (d, J=7.5 Hz, 2H), 7.49 (d, J=7.5 Hz, 2H), 7.43 (d, 1H, J=8.0 Hz), 7.32 (d, 2H, J=2.8 Hz), 6.96 (d, J=9.0 Hz, 2H), 6.75 (dd, 2H, J=9.5, 2.8 Hz), 5.69 (s, 2H), 4.69 (s, 2H), 3.28 (s, 12H), 0.66 (s, 3H), 0.60 (s, 3H).
$^{13}$C NMR (125 MHz, CD$_3$OD) δ 170.7, 167.0, 160.3, 160.0, 157.6, 149.8, 138.7, 138.6, 136.6, 135.7, 135.6, 133.2, 130.7, 128.4, 127.8, 127.3, 126.8, 124.7, 124.0, 116.5, 113.4, 93.2, 67.3, 43.1, 39.1, −1.0, −2.8.
HRMS (ESI): m/z calc. for C$_{40}$H$_{41}$N$_8$O$_4$Si 725.3020; found 725.3014 (−2.48 ppm), [M+H]$^+$.

B.2 SiR650-5CP (6.1 mg, 80%)

$^1$H NMR (400 MHz, CD$_3$OD) δ 9.36 (t, 1H, J=5.6 Hz), 8.72 (m, 1H), 8.23 (m, 1H), 7.43 (m, 5H), 7.32 (d, 2H, J=2.8 Hz), 6.96 (d, 2H, J=9.4 Hz), 6.76 (dd, 2H, J=9.5, 2.9 Hz), 6.13 (s, 1H), 5.38 (s, 2H), 4.68 (d, 2H, J=6.0 Hz), 3.34 (s, 12H), 0.66 (s, 3H), 0.60 (s, 3H).
$^{13}$C NMR (125 MHz, acetone-d$_6$) δ 170.9, 169.3, 165.0, 160.7, 157.4, 149.6, 139.5, 136.4, 135.9, 135.4, 133.4, 131.3, 128.5, 127.9, 127.8, 126.8, 124.7, 123.8, 116.6, 113.5, 95.3, 67.5, 43.0, 39.4, −0.5, −2.1.
HRMS (ESI): m/z calc. for C$_{39}$H$_{40}$ClN$_6$O$_4$Si 719.2569; found 719.2567 (−0.28 ppm), [M+H]$^+$.

B.3 SiR650-6BG (7.0 mg, 91%)

$^1$H NMR (400 MHz, DMSO-d$_6$) δ 9.36 (t, 1H, J=5.0 Hz), 8.50 (s, 1H), 8.14 (d, 1H, J=7.6 Hz), 8.07 (d, 1H, J=7.8 Hz), 7.71 (s, 1H), 7.49 (d, 2H, J=7.9 Hz), 7.34 (d, 2H, J=7.8 Hz), 7.05 (s, 2H), 6.66 (m, 4H), 5.52 (s, 2H), 4.45 (d, 2H, J=5.2 Hz), 2.95 (s, 12H), 0.63 (m, 3H), 0.53 (s, 3H).
$^{13}$C NMR (100 MHz, acetone-d$_6$) δ 169.2, 165.2, 159.9, 157.7, 155.5, 149.6, 139.6, 136.3, 131.4, 128.9, 128.8, 128.4, 128.0, 125.2, 123.1, 116.6, 113.7, 68.5, 65.2, 43.1, 39.4, 14.7, −0.6, −1.9.
HRMS (ESI): m/z calc. for C$_{40}$H$_{41}$N$_8$O$_4$Si 725.3020; found 725.3032 (1.65 ppm), [M+H]$^+$.

B.4 SiR650-6CP (5.8 mg, 76%)

$^1$H NMR (400 MHz, CD$_3$OD) δ 8.32 (d, 1H, J=8.2 Hz), 8.15 (dd, 1H, J=8.2, 1.7 Hz), 7.74 (d, 1H, J=1.4 Hz), 7.42-7.36 (m, 4H, J=8.3 Hz), 7.33 (d, 2H, J=2.7 Hz), 6.98 (d, 2H, J=9.5 Hz), 6.76 (dd, 2H, J=9.5, 2.8 Hz), 6.10 (s, 1H), 5.35 (s, 2H), 4.59 (s, 2H), 3.31 (s, 12H, overlapped with MeOH), 0.65 (s, 3H), 0.60 (s, 3H).
$^{13}$C NMR (125 MHz, acetone-d$_6$) δ 170.8, 169.3, 165.2, 160.7, 155.5, 149.6, 140.2, 139.2, 136.2, 135.4, 131.4, 128.5, 128.4, 128.0, 127.95, 127.9, 125.2, 123.2, 116.5, 113.6, 95.3, 67.5, 43.0, 39.4, −0.6, −1.9.
HRMS (ESI): m/z calc. for C$_{39}$H$_{40}$ClN$_6$O$_4$Si 719.2569; found 719.2575 (0.84 ppm), [M+H]$^+$.

B.5 SiRMe-5BG (4.8 mg, 63%; Comparative Example)

$^1$H NMR (400 MHz, CD$_3$OD) δ 9.20 (t, 1H, J=5.9 Hz), 8.27 (s, 1H), 7.94 (s, 1H), 7.89 (dd, 1H, J=7.9, 1.3 Hz), 7.58 (d, 2H, J=8.4 Hz), 7.47 (d, 2H, J=8.2 Hz), 7.40 (d, 2H, J=2.9 Hz), 7.28 (d, 1H, J=7.9 Hz), 7.06 (d, 2H, J=9.6 Hz), 6.79 (dd, 2H, J=9.6, 2.9 Hz), 5.67 (s, 2H), 4.68 (s, 2H), 3.36 (s, 12H), 2.12 (s, 3H), 0.64 (s, 3H), 0.62 (s, 3H).
$^{13}$C NMR (100 MHz, CD$_3$OD) δ 168.0, 167.8, 159.8, 154.4, 152.8, 148.1, 142.2, 141.5, 140.6, 139.5, 136.3, 134.7, 134.3, 129.2, 128.8, 128.8, 127.4, 126.7, 124.4, 121.0, 114.0, 69.1, 42.9, 39.5, 18.1, −2.5, −2.7.
HRMS (ESI): m/z calc. for C$_{40}$H$_{43}$N$_8$O$_2$Si 695.3278; found 695.3273 (−0.72 ppm), [M+H]$^+$.

B.6 SiRMe-5CP (5.0 mg, 66%; Comparative Example)

$^1$H NMR (400 MHz, CD$_3$OD) δ 7.93 (s, 1H), 7.89 (m, 1H), 7.44 (d, 2H, J=3.9 Hz), 7.39 (d, 2H, J=2.9 Hz), 7.27 (d, 1H, J=7.9 Hz), 7.07 (d, 2H, J=9.6 Hz), 6.80 (dd, 2H, J=9.6, 2.9 Hz), 6.13 (s, 1H), 5.38 (s, 2H), 4.66 (s, 2H), 3.37 (s, 12H), 2.12 (s, 3H), 0.64 (s, 3H), 0.62 (s, 4H).
$^{13}$C NMR (101 MHz, CD$_3$OD) δ 171.0, 167.9, 167.9, 154.4, 148.1, 142.2, 140.6, 138.8, 136.3, 135.4, 134.7, 129.2, 128.9, 128.2, 127.3, 126.7, 124.4, 120.9, 114.0, 95.2, 67.6, 43.0, 39.5, 18.1, −2.5, −2.7.
HRMS (ESI): m/z calc. for C$_{39}$H$_{42}$ClN$_6$O$_2$Si 689.2827; found 689.2839 (1.74 ppm), [M+H]$^+$.

B.7 SiRMe-6BG (3.9 mg, 51%; Comparative Example)

$^1$H NMR (400 MHz, CD$_3$OD) δ 8.29 (s, 1H), 7.99 (dd, 1H, J=8.0, 1.9 Hz), 7.67 (d, 1H, J=1.9 Hz), 7.54 (m, 3H), 7.42 (d, 2H, J=8.2 Hz), 7.40 (d, 2H, J=2.9 Hz), 7.06 (d, 2H, J=9.6 Hz), 6.79 (dd, 2H, J=9.7, 2.9 Hz), 5.64 (s, 2H), 4.59 (s, 2H), 3.37 (s, 12H), 2.12 (s, 3H), 0.63 (s, 6H).
$^{13}$C NMR (100 MHz, CD$_3$OD) δ 167.7, 167.6, 159.8, 154.4, 152.6, 148.1, 141.7, 140.7, 139.9, 139.5, 139.1, 134.2, 131.6, 130.3, 128.8, 127.7, 127.5, 127.3, 126.9, 120.9, 114.0, 69.2, 42.9, 39.5, 18.1, −2.6, −2.6.
HRMS (ESI): m/z calc. for C$_{40}$H$_{43}$N$_8$O$_2$Si 695.3278; found 695.3277 (−0.14 ppm), [M+H]$^+$.

B.8 SiRMe-6CP (5.5 mg, 72%; Comparative Example)

$^1$H NMR (400 MHz, CD$_3$OD) δ 9.08 (t, 1H, J=5.3 Hz), 7.99 (dd, 1H, J=8.0, 1.8 Hz), 7.66 (d, 1H, J=1.7 Hz), 7.55 (d, 1H, J=8.0 Hz), 7.39 (m, 6H), 7.07 (d, 2H, J=9.7 Hz), 6.80 (dd, 2H, J=9.7, 2.9 Hz), 6.10 (s, 1H), 5.35 (s, 2H), 4.59 (d, 2H, J=5.7 Hz), 3.37 (s, 12H), 2.12 (s, 3H), 0.63 (s, 6H).
$^{13}$C NMR (100 MHz, CD$_3$OD) δ 171.0, 167.9, 167.6, 154.8, 148.2, 140.7, 139.8, 139.1, 138.8, 135.4, 131.7, 130.3, 128.1, 127.8, 127.4, 127.0, 120.9, 114.0, 95.3, 67.6, 43.0, 39.5, 18.1, −2.6, −2.6.
HRMS (ESI): m/z calc. for C$_{39}$H$_{42}$ClN$_6$O$_2$Si 689.2827; found 689.2822 (−0.73 ppm), [M+H]$^+$.

C. Live Cell Staining

Figure 2:
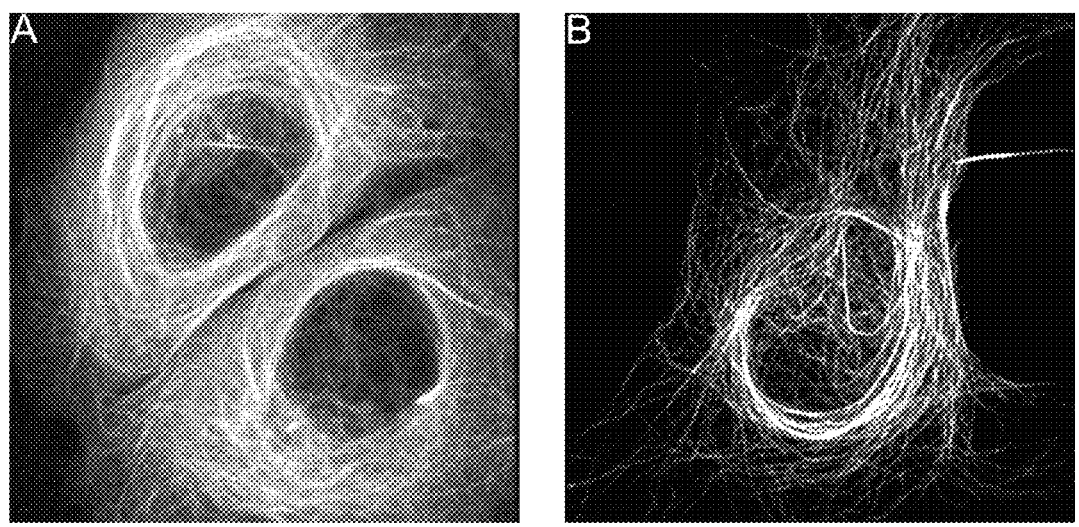
FIG. 2: Labeling of SNAP fusions with compounds according to the invention in living cells.

As a representative example for the labeling of a SNAP-tag fusion with BG-Sir650, the labeling and fluorescence imaging of SNAP-Cep41 (microtubule binding protein) fusion protein in U2OS cells is described. SNAP-Cep41 was expressed from episomal pEBTet plasmid encoding puromycin resistance under a doxycycline inducible promoter in U2OS cells. Prior to induction of expression, cells were selected by growing them in complete Dulbecco's Modified Eagle's Medium (DMEM) with 1 µg/ml puromycin for at least 1.5 weeks. SNAP-Cep41 fusion protein expression was induced for 48 h by adding to complete DMEM grow medium doxycycline at final concentration of 0.1 µg/ml before staining procedure. Living cells were stained by replacing old media with complete DMEM growth media containing 5 µM BG-SiR650, and incubated for 30 min at 37° C. in 5% $CO_2$ incubator. Cells were washed two times with Hank's Buffered Salt Solution (HBSS) for 5 min and once with media for 1 h. Before imaging, growth media was replaced with HBSS. Images (FIG. 2A) were acquired on a confocal fluorescence microscope as z-stacks and presented as maximum intensity projections. For the imaging of fixed cells, living cells were labeled with 1 µM BG-Sir650 for 30 min at 37° C. Cells were pre-extracted with BRB80 buffer containing 0.2% NP-40 and fixed with MeOH/EGTA at −20° C. for 5 min. Fixed cells were mounted in 90% glycerol containing 5% n-propyl-gallate as antifading. Images (FIG. 2B) were acquired on a confocal fluorescence microscope as z-stack and presented as maximum intensity projections. The image shown in FIG. 2B has been deconvolved using Huygens Essential software.

D. Photostability of the Dyes

Figure 3:
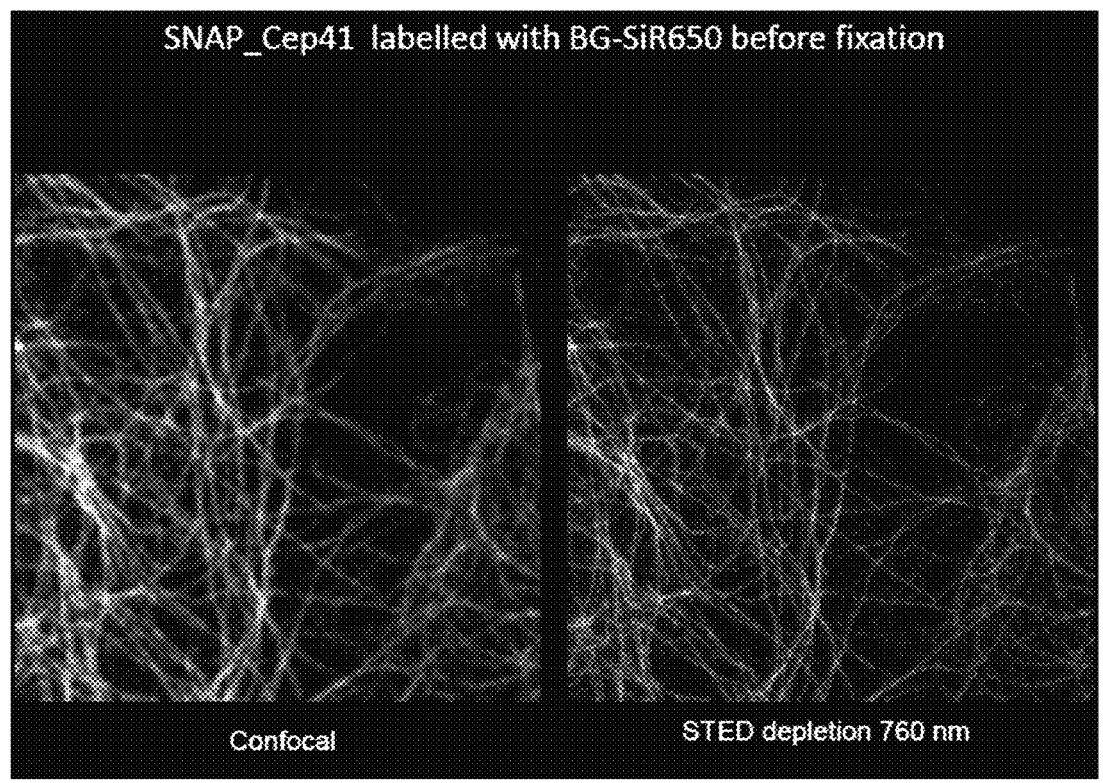
FIG. 3: Superresolution microscopy application of a compound according to the invention.

Comparative experiments of prior art dyes and a compound according to the invention are exemplarily outlined in FIG. 3. A. mAB-Alexa647 is goat anti-mouse IgG-Alexa Fluor 647 (highly cross-absorbed), purchased from Invitrogen (A-21236); mAb-Atto647N is goat anti-rabbit IgG-Atto647N (STED), purchased from Active Motif (15048); BG-SiR650 is B.3.
Imaging conditions on Zeiss LSM 710 were as follows:
Objective: Plan-Apochromat 63×/1.00 Oil DIC M27
Pixel Size: 22×22 nm
Pinhole: 30 µm (0.5-0.6 AU)
Averaging: 8
Zoom: 24
633 nm laser: 3% (36 µW reaching the objective, measured)
Detection interval: 640-758 nm
Mounting media: 86% glycerol+4% NPG in 1×PBS (Lonza)
As is readily apparent, the compound according to the invention possesses outstanding photostability, comparable to mAb-Atto647N.

The invention claimed is:
1. A compound of formula:

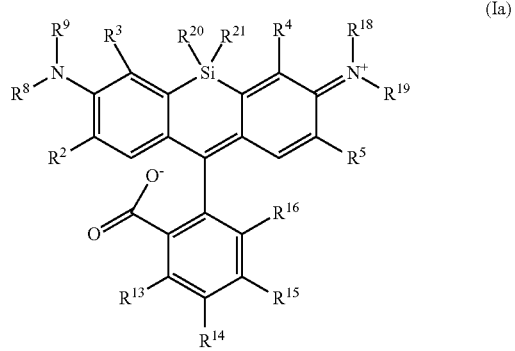

(Ia)

its corresponding spirolactone and its alternative protonation stages comprising negatively or positively charged counterions;

wherein for (Ia), the corresponding spirolactone and the alternative protonation stages:

$R^2$, $R^3$, $R^4$ and $R^5$ are independently, respectively, one of: hydrogen; $C_1$-$C_6$ alkyl, F, Cl, and Br;

$R^8$, $R^9$, $R^{18}$ and $R^{19}$ are independently substituents;

each of $R^{13}$, $R^{14}$, $R^{15}$ and $R^{16}$ are independently, respectively, one of: H; F; Cl; Br; I; $SO_3X$, wherein X is H or a counterion; a carboxylic acid, a salt of a carboxylic acid, an ester of a carboxylic acid, an amide, CN, nitro, hydroxyl, azido, amino, hydrazine, and $R^{20}$ and $R^{21}$ are independently Hydrogen; $C_1$-$C_6$-alkyl, either saturated or unsaturated; C1-C6 alkoxy; or aryl, wherein the alkyl, alkoxy, or aryl portions have one or more substituents chosen from the group consisting of F, Cl, Br, I.

2. The compound of claim 1, wherein
$R^8$, $R^9$, $R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, and each aforementioned alkyl is optionally substituted with F, amino, hydroxyl, a carboxylic acid, a salt of a carboxylic acid, or a carboxylic acid ester or a $C_1$-$C_6$ alkyl; OR
$R^8$ in combination with $R^9$ and/or $R^{18}$ in combination with $R^{19}$ form a five- or six-membered heterocyclic substructure chosen from the group consisting of piperidines, morpholines, pyrrolidines or piperazines, and each of the aforementioned heterocyclic substructures is optionally substituted by F, methyl, a carboxylic acid, a salt of a carboxylic acid or a carboxylic acid ester or a $C_1$-$C_6$ alkyl.

3. A compound of formula:

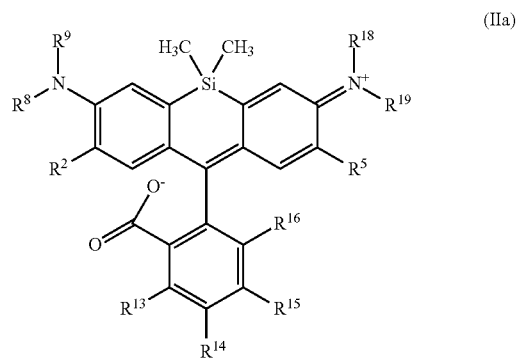

(IIa)

its corresponding spirolactone and its alternative protonation stages comprising negatively or positively charged counterions;

wherein for (IIa), the corresponding spirolactone and the alternative protonation stages:
each of $R^{13}$, $R^{14}$, $R^{15}$ and $R^{16}$ are independently, respectively, one of: H, F, Cl, Br, I, $SO_3X$, a carboxylic acid, a salt of a carboxylic acid, an ester of a carboxylic acid, an amide, CN, nitro, hydroxyl, azido, amino, hydrazine;

$R^8$ or $R^9$ in combination with $R^2$ forms a substructure

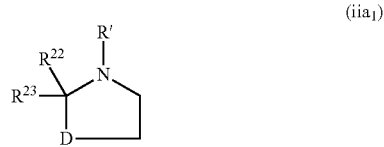
(iia$_1$)

wherein
R' denotes the respective one of $R^8$ and $R^9$ which is not incorporated into the ring of substructure (iia$_1$) and
R' is H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, and each aforementioned alkyl is optionally substituted with F, amino, hydroxyl, a carboxylic acid, a salt of a carboxylic acid, or a carboxylic acid ester or a $C_1$-$C_6$ alkyl;
D represents O; S; or —C($R^{24}$)($R^{25}$)-, with $R^{24}$ and $R^{25}$ being independently chosen from the group consisting of hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$ or $C_6$ alkynyl, branched or linear; $C_1$-$C_6$ substituted alkynyl, branched or linear; aryl; substituted aryl; hydroxyl; halogen; alkoxyl; carboxyl; and and/or $R^{18}$ or $R^{19}$ in combination with $R^5$ forms a substructure

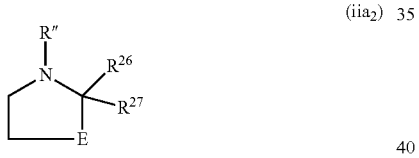
(iia$_2$)

R" denotes the respective one of $R^{18}$ and $R^{19}$ which is not incorporated into the ring of substructure (iia$_2$) and
R" is H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, and each aforementioned alkyl is optionally substituted with F, amino, hydroxyl, a carboxylic acid, a salt of a carboxylic acid, or a carboxylic acid ester or a $C_1$-$C_6$ alkyl;
E represents O; S; or —C($R^{28}$)($R^{29}$)—, with $R^{28}$ and $R^{29}$ being independently chosen from the group consisting of hydrogen; $C_1$-$C_6$ alkyl, branched or linear; $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl; and
$R^{22}$, $R^{23}$, $R^{26}$ and $R^{27}$ are independently hydrogen, $C_1$-$C_6$ alkyl, branched or linear $C_1$-$C_6$ substituted alkyl, branched or linear, in particular F substituted $C_1$-$C_6$ alkyl, branched or linear; $C_1$-$C_6$ alkenyl, branched or linear; $C_1$-$C_6$ substituted alkenyl, branched or linear; $C_1$-$C_6$ alkynyl, branched or linear; $C_1$-$C_6$ substituted alkynyl, branched or linear; aryl; substituted aryl; hydroxyl; halogen; alkoxyl; carboxyl substituents.

4. The compound of claim 1, wherein at least one of $R^2$, $R^3$, $R^4$, $R^5$, $R^8$, $R^9$, $R^{13}$, $R^{14}$, $R^{15}$, $R^{16}$, $R^{18}$, $R^{19}$, $R^{20}$ and $R^{21}$ is -L-R*, wherein
each L independently is a covalent linkage, each or some of the L being the same or different;
each R* is independently chosen from the group consisting of acrylamide; an activated ester of a carboxylic acid; a hydroxyl; an anhydride of a carboxylic acid; an aldehyde; an alkyl halide; a sulfonate; an amine; an anhydride; an aniline; an aryl halide; an azide; an alkyne; a boronate; a carboxylic acid; a carbodiimide; a diazoalkane; an epoxide; a glycol; a haloacetamide; a halotriazine; a hydrazine; a hydroxylamine; an imido ester; an isocyanate; an isothiocyanate; a ketone; a maleimide; a phosporamidite; a sulfonyl halide; a thiol; an alkyne; a phosphine; a sulfonyl ester —CH$_2$OSO$_2$R, wherein R is $C_6H_4CH_3$ (tosyl), $CH_3$ (mesyl), $CF_3$ (triflate) or $CF_2CF_3$ (nonaflate).

5. The compound of claim 3, wherein at least one of $R^2$, $R^5$, $R^8$, $R^{13}$, $R^{14}$, $R^{15}$, $R^{16}$, $R^{18}$ and $R^{19}$ is -L-R*,
each L independently is a covalent linkage, each or some of the L being the same or different;
each R* is independently chosen from the group consisting of acrylamide; an activated ester of a carboxylic acid; a hydroxyl; an anhydride of a carboxylic acid; an aldehyde; an alkyl halide; a sulfonate; an amine; an anhydride; an aniline; an aryl halide; an azide; an alkyne; a boronate; a carboxylic acid; a carbodiimide; a diazoalkane; an epoxide; a glycol; a haloacetamide; a halotriazine; a hydrazine; a hydroxylamine, an imido ester; an isocyanate; an isothiocyanate; a ketone; a maleimide; a phosporamidite; a sulfonyl halide; a thiol; an alkyne; a phosphine; a sulfonyl ester —CH$_2$OSO$_2$R, and R is $C_6H_4CH_3$ (tosyl), $CH_3$ (mesyl), $CF_3$ (triflate) or $CF_2CF_3$ (nonaflate).

6. The compound of claim 1, wherein at least one of $R^2$, $R^3$, $R^4$, $R^5$, $R^8$, $R^9$, $R^{13}$, $R^{14}$, $R^{15}$, $R^{16}$, $R^{18}$, $R^{19}$, $R^{20}$ and $R^{21}$ is -L'-Y,
each L' independently is a covalent linkage, each or some the same or different;
each Y independently is an amino acid; a peptide; a protein; a monosaccharide; a disaccharide; a polysaccharide; a calcium-complexing group; a lanthanide-complexing group; a nickel-complexing group; a cobalt-complexing group; ethylenediamine tetraacetic acid; nitriloacetic acid; a nucleotide; a substrate of an enzyme; an irreversible inhibitor of an enzyme forming a covalent bond with an enzyme; an agonist of a receptor; a ligand that binds with a KD of at least 10 μM to a nucleic acid; a ligand that binds with a KD of at least 10 μM to a protein; a substrate of SNAP-tag; a substrate of CLIP-tag; a substrate of Halo-tag, a ligand binding to dihydrofolate reductase; methotrexate; trimethoprim; a substrate of biotin ligase; a substrate of phosphopantetheine transferase; a substrate of lipoic acid ligase; biotin; a ligand binding to streptavidin, avidin or neutravidin; a cofactor of an enzyme; a hormone; a toxin; a fluorophore; a nucleic acid polymer; a hapten; an antigen; a drug; a lipid; a lipid assembly; a non-biological organic polymer; a polymeric microparticle; an animal cell, a plant cell; a bacterium, a yeast; a virus; a protist.

7. The compound of claim 3; wherein at east one of $R^2$, $R^5$, $R^8$, $R^9$, $R^{13}$, $R^{14}$, $R^{15}$, $R^{16}$, $R^{18}$ and $R^{19}$ is -L'-Y,
each L' independently is a covalent linkage, each or some the same or different;

each Y independently is an amino acid; a peptide; a protein; a monosaccharide; a disaccharide; a polysaccharide; a calcium-complexing group; a lanthanide-complexing group; a nickel-complexing group; a cobalt-complexing group: ethylenediamine tetraacetic acid; nitriloacetic acid; a nucleotide; a substrate of an enzyme; an irreversible inhibitor of an enzyme forming a covalent bond with an enzyme; an agonist of a receptor; a ligand that binds with a KD of at least 10 µM to a nucleic acid; a ligand that binds with a KD of at least 10 µM to a protein; a substrate of SNAP-tag; a substrate of CLIP-tag; a substrate of Halo-tag, a ligand binding to dihydrofolate reductase; methotrexate; trimethoprim; a substrate of biotin ligase; a substrate of phosphopantetheine transferase; a substrate of lipoic acid ligase; biotin; a ligand binding to streptavidin, avidin or neutravidin; a cofactor of an enzyme; a hormone; a toxin; a fluorophore; a nucleic acid polymer; a hapten; an antigen; a drug; a lipid; a lipid assembly; a non-biological organic polymer; a polymeric microparticle; an animal cell, a plant cell; a bacterium, a yeast; a virus; a protist.

8. The compound of claim 4, wherein L is independently a single covalent bond, or L is a covalent linkage having 1-24 non-hydrogen atoms selected from the group consisting of C, N, O, P and S and is composed of any combination of single, double, triple or aromatic carbon-carbon bonds, carbon-nitrogen bonds, nitrogen-nitrogen bonds, carbon-oxygen bonds, carbon-sulfur bonds, phosphorous-oxygen bonds and phosphorous-nitrogen bonds.

9. The compound of claim 5, wherein L is independently a single covalent bond, or L is a covalent linkage having 1-24 non-hydrogen atoms selected from the group consisting of C, N, O, P and S and is composed of any combination of single, double, triple or aromatic carbon-carbon bonds, carbon-nitrogen bonds, nitrogen-nitrogen bonds, carbon-oxygen bonds, carbon-sulfur bonds, phosphorous-oxygen bonds and phosphorous-nitrogen bonds.

10. The compound of claim 6, wherein L' is independently a single covalent bond, or L' is a covalent linkage having 1-24 non-hydrogen atoms selected from the group consisting of C, N, O, P and S and is composed of any combination of single, double, triple or aromatic carbon-carbon bonds, carbon-nitrogen bonds, nitrogen-nitrogen bonds, carbon-oxygen bonds, carbon-sulfur bonds, phosphorous-oxygen bonds and phosphorous-nitrogen bonds.

11. The compound of claim 7, wherein L' is independently a single covalent bond, or L' is a covalent linkage having 1-24 non-hydrogen atoms selected from the group consisting of C, N, O, P and S and is composed of any combination of single, double, triple or aromatic carbon-carbon bonds, carbon-nitrogen bonds, nitrogen-nitrogen bonds, carbon-oxygen bonds, carbon-sulfur bonds, phosphorous-oxygen bonds and phosphorous-nitrogen bonds.

12. The compound of claim 4, wherein the compound is utilized to label a specific target by reacting the compound with a substrate molecule that binds or can be enzymatically coupled to said target, in particular a protein or peptide, and the reaction occurs between the substrate molecule and the compound at least at one of $R^{13}$, $R^{14}$ and $R^{15}$, thereby establishing a binding moiety towards a specific target at least at one $R^{13}$, $R^{14}$ and $R^{15}$.

13. The compound of claim 5, wherein the compound is utilized to label a specific target by reacting the compound with a substrate molecule that binds or can be enzymatically coupled to said target, in particular a protein or peptide, and the reaction occurs between the substrate molecule and the compound at least at one of $R^{13}$, $R^{14}$ and $R^{15}$, thereby establishing a binding moiety towards a specific target at least at one $R^{13}$, $R^{14}$ and $R^{15}$.

14. The compound according to claim 12, wherein the specific target, in particular the protein or peptide, on the one hand, and the binding moieties, on the other hand, are chosen from the group consisting of SNAP-tag and benzylguanine; CLIP-tag and benzylcytosine; HALO-tag and 1° chloride; dihydrofolate reductase and trimethoprim; kinase and kinase inhibitor; DNA polymerase and its substrates.

15. The compound according to claim 13, wherein the specific target, in particular the protein or peptide, on the one hand, and the binding moieties, on the other hand, are chosen from the group consisting of SNAP-tag and benzylguanine; CLIP-tag and benzylcytosine; HALO-tag and 1° chloride; dihydrofolate reductase and trimethoprim; kinase and kinase inhibitor; DNA polymerase and its substrates.

16. The compound according to claim 12, wherein the substrate can be enzymatically bound to the target by an enzyme chosen from the group consisting of phosphopantetheine transferase, biotin ligase, liopoic acid ligase; DNA polymerase; DNA methyltransferase.

17. The compound according to claim 13, wherein the substrate can be enzymatically bound to the target by an enzyme chosen from the group consisting of phosphopantetheine transferase, biotin ligase, liopoic acid ligase; DNA polymerase; DNA methyltransferase.

18. The compound of claim 4, wherein the compound is utilized to provide a binding agent for a specific target, in particular a protein, a peptide or a nucleic acid, and the compound is reacted at least at one of $R^{13}$, $R^{14}$ and $R^{15}$, with a substrate molecule that binds or can be enzymatically coupled to said specific target.

19. The compound of claim 5, wherein the compound is utilized to provide a binding agent for a specific target, in particular a protein, a peptide or a nucleic acid, and the compound is reacted at least at one of $R^{13}$, $R^{14}$ and $R^{15}$, with a substrate molecule that binds or can be enzymatically coupled to said specific target.

20. The compound of claim 1, wherein the compound is part of a kit-of-parts, the kit-of-parts further comprises at least one of:
   I) a second compound that is able to bind to a specific target, in particular a protein or a peptide, and which second compound is able to react with Ia), at least at one of $R^{13}$, $R^{14}$ and $R^{15}$;
   ii) an activating agent to allow for the reaction of either Ia) or the reaction product of Ia) and ii) with a specific target to occur; and
   iii) instructions for use of the kit-of-parts.

21. The compound of claim 3, wherein the compound is part of a kit-of-parts, the kit-of-parts further comprising at least one of:
   I) a second compound that is able to bind to a specific target, in particular a protein or a peptide, and which second compound is able to react with IIa), at least at one of $R^{13}$, $R^{14}$ and $R^{15}$;
   ii) an activating agent to allow for the reaction of either IIa) or the reaction product of IIa) and ii) with a specific target to occur; and
   iii) instructions for use of the kit-of-parts.

22. The compound of claim 1, wherein the compound is utilized in labelling of proteins or nucleic acids in vitro, in living cells or in living organisms, by attaching the compound to the protein or nucleic acid.

23. The compound of claim 3, wherein the compound is utilized in labelling of proteins or nucleic acids in vitro, in living cells or in living organisms, by attaching the compound to the protein or nucleic acid.

24. The compound of claim 1, wherein the compound is detected by a method chosen from the group of fluorescence spectroscopy; fluorescence microscopy; fluorescence imaging; stochastic optical reconstruction microscopy (STORM); direct STORM (dSTORM); ground state depletion microscopy followed by individual molecule return (GSDIM); ground state depletion (GSD) microscopy; single-molecule spectroscopy; Förster resonance energy transfer (FRET) applications, in particular time-resolved; fluorescence correlation spectroscopy; fluorescence anisotropy spectroscopy; correlative fluorescence-electron microscopy; fluorescence activated cell sorting; oxygen, fluoride or glycerol sensing in vitro, in living cells or living organisms.

25. The compound of claim 3, wherein the compound is detected by a method chosen from the group of fluorescence spectroscopy; fluorescence microscopy; fluorescence imaging; stochastic optical reconstruction microscopy (STORM); direct STORM (dSTORM); ground state depletion microscopy followed by individual molecule return (GSDIM); ground state depletion (GSD) microscopy; single-molecule spectroscopy; Förster resonance energy transfer (FRET) applications, in particular time-resolved; fluorescence correlation spectroscopy; fluorescence anisotropy spectroscopy; correlative fluorescence-electron microscopy; fluorescence activated cell sorting; oxygen, fluoride or glycerol sensing in vitro, in living cells or living organisms.

* * * * *